US009216183B2

(12) United States Patent
Ahluwalia et al.

(10) Patent No.: US 9,216,183 B2
(45) Date of Patent: *Dec. 22, 2015

(54) TOPICAL TREATMENT FOR CHEMOTHERAPY INDUCED EYELASH LOSS OR HYPOTRICHOSIS USING PROSTAMIDE F2 ALPHA AGONISTS

(71) Applicant: ALLERGAN, INC., Irvine, CA (US)

(72) Inventors: Gurpreet Ahluwalia, Orange, CA (US); Frederick C. Beddingfield, Pacific Palisades, CA (US); Sydney Edwards, Aliso Viejo, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,394

(22) Filed: Apr. 11, 2014

(65) Prior Publication Data
US 2014/0221493 A1 Aug. 7, 2014

Related U.S. Application Data

(63) Continuation-in-part of application No. 14/199,402, filed on Mar. 6, 2014, which is a continuation of application No. 13/738,732, filed on Jan. 10, 2013, now Pat. No. 8,758,733, and a continuation-in-part of application No. 13/937,512, filed on Jul. 9, 2013, now Pat. No. 8,926,953, which is a continuation of application No. 13/441,783, filed on Apr. 6, 2012, now Pat. No. 8,632,760, which is a continuation of application No. 13/356,284, filed on Jan. 23, 2012, now Pat. No. 8,263,054, which is a continuation of application No. 12/425,933, filed on Apr. 17, 2009, now Pat. No. 8,298,518, which is a continuation of application No. 11/943,714, filed on Nov. 21, 2007, now Pat. No. 8,038,988, which is a continuation of application No. 11/805,122, filed on May 22, 2007, now Pat. No. 8,101,161, which is a continuation of application No. 10/345,788, filed on Jan. 15, 2003, now Pat. No. 7,351,404.

(60) Provisional application No. 61/611,920, filed on Mar. 16, 2012, provisional application No. 61/584,877, filed on Jan. 10, 2012, provisional application No. 60/354,425, filed on Feb. 4, 2002.

(51) Int. Cl.
| | |
|---|---|
| A61K 8/00 | (2006.01) |
| A61K 31/5575 | (2006.01) |
| A61K 8/42 | (2006.01) |
| A61K 8/49 | (2006.01) |
| A61Q 1/10 | (2006.01) |
| A61K 8/63 | (2006.01) |
| A61Q 7/00 | (2006.01) |
| A61K 9/00 | (2006.01) |
| A61K 31/165 | (2006.01) |
| A61K 9/08 | (2006.01) |

(52) U.S. Cl.
CPC ............... *A61K 31/5575* (2013.01); *A61K 8/42* (2013.01); *A61K 8/4953* (2013.01); *A61K 8/63* (2013.01); *A61K 9/0014* (2013.01); *A61K 9/08* (2013.01); *A61K 31/165* (2013.01); *A61Q 1/10* (2013.01); *A61Q 7/00* (2013.01); *A61K 9/0048* (2013.01); *A61K 2800/10* (2013.01)

(58) Field of Classification Search
CPC .................................................. A61K 2800/10
See application file for complete search history.

(56) References Cited

U.S. PATENT DOCUMENTS

| | | | |
|---|---|---|---|
| 3,382,247 | A | 5/1968 | Anthony et al. |
| 3,644,363 | A | 2/1972 | Kim |
| 4,128,577 | A | 12/1978 | Nelson |
| 4,139,619 | A | 2/1979 | Chidsey |
| 4,311,707 | A | 1/1982 | Birnbaum et al. |
| 4,543,353 | A | 9/1985 | Faustini et al. |
| 4,596,812 | A | 6/1986 | Chidsey et al. |
| 4,599,353 | A | 7/1986 | Bito |
| 4,812,457 | A | 3/1989 | Narumiya et al. |
| 4,839,342 | A | 6/1989 | Kaswan |
| 4,883,581 | A | 11/1989 | Dickakian |
| 4,888,354 | A | 12/1989 | Chang et al. |
| 4,889,845 | A | 12/1989 | Ritter et al. |
| 4,952,581 | A | 8/1990 | Bito et al. |
| 4,968,812 | A | 11/1990 | Wang et al. |
| 5,001,153 | A | 3/1991 | Ueno et al. |
| 5,194,429 | A | 3/1993 | Ueno et al. |

(Continued)

FOREIGN PATENT DOCUMENTS

| | | |
|---|---|---|
| AU | 2008203212 | 10/2008 |
| AU | 2010227111 | 11/2010 |

(Continued)

OTHER PUBLICATIONS

U.S. Appl. No. 90/009,431, filed Mar. 10, 2009, Murray Johnstone.

(Continued)

*Primary Examiner* — Paul Dickinson
(74) *Attorney, Agent, or Firm* — Lorenz Siddiqi

(57) ABSTRACT

The present invention is directed to compositions and methods for the treatment of post-chemotherapeutic hypotrichosis. More specifically, the present invention is directed to the use of compositions comprising bimatoprost for the treatment of post-chemotherapeutic hypotrichosis which may be applied before, during and after receiving chemotherapeutic treatment.

20 Claims, 13 Drawing Sheets

(56) References Cited

U.S. PATENT DOCUMENTS

| | | | |
|---|---|---|---|
| 5,280,018 | A | 1/1994 | Ritter et al. |
| 5,288,754 | A | 2/1994 | Woodward et al. |
| 5,296,504 | A | 3/1994 | Stjernschantz et al. |
| 5,321,128 | A | 6/1994 | Stjernschantz et al. |
| 5,352,708 | A | 10/1994 | Woodward et al. |
| 5,422,368 | A | 6/1995 | Stjernschantz et al. |
| 5,422,369 | A | 6/1995 | Stjernschantz et al. |
| 5,431,881 | A | 7/1995 | Palacios |
| 5,474,979 | A | 12/1995 | Ding et al. |
| 5,480,900 | A | 1/1996 | DeSantis et al. |
| 5,508,303 | A | 4/1996 | Isogaya et al. |
| 5,510,383 | A | 4/1996 | Bishop et al. |
| 5,545,655 | A | 8/1996 | Friedlander et al. |
| 5,578,618 | A | 11/1996 | Stjernschantz et al. |
| 5,578,643 | A | 11/1996 | Hanson et al. |
| 5,607,978 | A | 3/1997 | Woodward et al. |
| 5,688,819 | A | 11/1997 | Woodward |
| 5,698,733 | A | 12/1997 | Hellberg et al. |
| 5,773,472 | A | 6/1998 | Stjernschantz et al. |
| 5,789,244 | A | 8/1998 | Heidrun et al. |
| 6,025,392 | A | 2/2000 | Selliah et al. |
| 6,124,344 | A | 9/2000 | Burk |
| 6,160,129 | A | 12/2000 | Burk |
| 6,203,782 | B1 | 3/2001 | Eliaz et al. |
| 6,232,344 | B1 | 5/2001 | Feng et al. |
| 6,254,860 | B1 | 7/2001 | Garst |
| 6,258,844 | B1 | 7/2001 | Garst et al. |
| 6,262,105 | B1 | 7/2001 | Johnstone |
| 6,350,442 | B2 | 2/2002 | Garst |
| 6,403,649 | B1 | 6/2002 | Woodward |
| 6,441,047 | B2 | 8/2002 | DeSantis |
| 7,351,404 | B2 | 4/2008 | Woodward et al. |
| 7,368,436 | B2 | 5/2008 | Gleave et al. |
| 7,388,029 | B2 | 6/2008 | DeLong et al. |
| 7,514,474 | B1 | 4/2009 | Lipkin et al. |
| 8,038,988 | B2 | 10/2011 | Woodward et al. |
| 8,101,161 | B2 | 1/2012 | Woodward et al. |
| 8,298,518 | B2 | 10/2012 | Woodward et al. |
| 8,926,953 | B2 | 1/2015 | Woodward et al. |
| 8,986,715 | B2 | 3/2015 | Woodward et al. |
| 2002/0044953 | A1 | 4/2002 | Michelet et al. |
| 2002/0103255 | A1 | 8/2002 | Hellberg et al. |
| 2002/0172693 | A1 | 11/2002 | DeLong et al. |
| 2003/0083381 | A1 | 5/2003 | Kumagai et al. |
| 2003/0147823 | A1 | 8/2003 | Woodward et al. |
| 2003/0199590 | A1 | 10/2003 | Cagle et al. |
| 2004/0052760 | A1 | 3/2004 | Michelet et al. |
| 2005/0222232 | A1 | 10/2005 | Delong et al. |
| 2007/0078175 | A1 | 4/2007 | Boulle et al. |
| 2007/0160562 | A1 | 7/2007 | Brinkenhoff |
| 2008/0070988 | A1 | 3/2008 | Woodward et al. |
| 2008/0275118 | A1 | 11/2008 | Shaw et al. |
| 2009/0018204 | A1 | 1/2009 | Brinkenhoff |
| 2009/0270392 | A1 | 10/2009 | Old et al. |
| 2011/0002866 | A1 | 1/2011 | Lubit et al. |
| 2011/0112198 | A1 | 5/2011 | Gore et al. |
| 2014/0194450 | A1 | 7/2014 | Ahluwalia et al. |
| 2014/0221493 | A1 | 8/2014 | Ahluwalia et al. |

FOREIGN PATENT DOCUMENTS

| | | |
|---|---|---|
| CA | 1208560 | 7/1986 |
| CA | 2144967 | 3/1994 |
| CA | 2174655 | 4/1995 |
| CA | 1339132 | 7/1997 |
| EP | 0170258 | 2/1986 |
| EP | 0249194 | 12/1987 |
| EP | 0308135 | 3/1989 |
| EP | 0639563 | 2/1995 |
| EP | 2802331 | 11/2014 |
| FR | 2239458 | 7/1973 |
| JP | S49-069636 | 7/1974 |
| JP | 61-218510 | 9/1986 |
| JP | H05-0331025 | 12/1993 |
| JP | H09-295921 | 11/1997 |
| JP | 10-287532 | 10/1998 |
| WO | 89-03384 | 4/1989 |
| WO | 95-11003 | 4/1995 |
| WO | 97-31895 | 9/1997 |
| WO | 98-33497 | 8/1998 |
| WO | 99-12895 | 3/1999 |
| WO | 00-54810 | 9/2000 |
| WO | 01-74307 | 10/2001 |
| WO | 01-74315 | 10/2001 |
| WO | 2007-143568 | 12/2007 |
| WO | 2009-011744 | 1/2009 |
| WO | 2011-119748 | 9/2011 |
| WO | 2012-068515 | 5/2012 |
| WO | 2013106565 | 7/2013 |

OTHER PUBLICATIONS

U.S. Appl. No. 90/009,430, filed Mar. 15, 2009, David Woodward.

Abramovitz, Mark et al, The Utilization of Recombinant prostanoid Receptors to Determine the Affinities and Selectivities of Prostaglandins and Related Analogs, Biochimica et Biophysica Acta, 2000, 285-293, 1483.

Abramovitz, Mark, Cloning and Expressing of a cDNA for the Human prostanoid FP Receptor, Journal of Biological Chemistry, 1994, 2632-2636, 269(4).

Adis Data Information, ZD 6416, 2003.

Adis, Alprostadil (NexMed) Alprox-TDTM, BefarTM, FemproxTM, Prostaglandin E1 (NewMed), Adis R & D Profile, 1999, 413-414, 2(6), Adis International Limited.

Al-Sereiti, M.R., Pharmacology of Rosemary (*Rosmarinus officinalis* Linn.) and its Therapeutic Potentials, Indian Journal of Experimental Biology, 1999, 124-130, 37.

Allergan Clinical Study Report, 192024-008, 2000.

Allergan, Inc., Dermatologic and Ophthalmic Drugs Advisory Committee Briefing Document for Bimatoprost Solution 0.03%, Dermatologic and Ophthalmic Drugs Advisory Committee Briefing Document for Bimatoprost Solution 0.03%, Oct. 29, 2008, 1-108.

Alm, Albert et al, Effects on Intraocular Pressure and Side Effects of 0.005% Latanoprost Applied Once Daily, Evening or Morning, Ophthalmology, 1995, 1743-1752, 102.

Alm, Albert et al, Phase III Latanoprost Studies in Scandinavia, the United Kingdom and the United States, Survey of Ophthalmology, Feb. 1997, S105-S110, 41(2).

Alm, Albert et al, Uveoscleral Outflow—A Review, Experimental Eye Research, 2009, 760-768, 88(4).

Alm, Albert, The Potential of Prostaglandin Derivates in Glaucoma Therapy, Current Opinion in Ophthalmology, 1993, 44-50, 4(11).

Audoly, Laurent et al, Identification of Specific EP Receptors Responsible for the Hemodynamic Effects of PGE2, Am. J. Physiol., 1999, H924-H930, 277.

Badawy, Sherif et al, Salt Selection for Pharmaceutical Compounds, Preformulation in Solid Dosage Form Development (Informa Healthcare), 2008, 63-80, Chapter 2.3, Adeyeyem, Moji, ed.

Bartmann, W., Synthesis and Biological Activity, Luteolytic Prostaglandins, Feb. 1979, 301-311, 17(2).

Bastin, Richard et al, Salt Selection and Optimisation Procedures for Pharmaceutical New Chemical Entities, Organic Process Research & Development, 2000, 427-435, 4.

Bean, Gerald, Commercially Available Prostaglandin Analogs for the Reduction of Intraocular Pressure: Similarities and Differences, Survey of Ophthalmology, 2008, S69-S84, 53 (Supp. 1).

Beisecker, Analee et al, Side Effects of Adjuvant Chemotherapy: Perceptions of Node-Negative Breast Cancer Patients, Psycho-Oncology, 1997, 85-93, 6.

Berge, Stephen M., Pharmaceutical Salts, Journal of Pharmaceutical Sciences, Jan. 1977, 1-19, 66 (1), US.

Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.

Bito, L.Z. et al, Long-Term Maintenance of Reduced Intraocular Pressure by Daily or Twice Daily Topical Application of

(56) References Cited

OTHER PUBLICATIONS

Prostaglandins to Cat or Rhesus Monkey Eyes, Investigative Ophthalmology & Visual Science, 1983, 312-319, 24(3).
Bito, Laszlo, A new approach to the medical management of glaucoma, from the bench to the clinic, and beyond, Investigative Ophthalmology & Visual Science, 2001, 1126-1133, 42(6), The Proctor Lecture.
Block, Lawrence, Medicated Applications, Remington's Pharmaceutical Sciences, 1985, 1567-1578, 17th Edition, Chapter 88.
Botchkarev, Vladimir, Molecular Mechanisms of Chemotherapy-Induced Hair Loss, JID Symposium Proceedings, 2003, 72-75, 8.
Brandt, James et al, Comparison of Once- or Twice-Daily Bimatoprost with Twice-Daily Timolol in Patients with Elevated IOP, American Academy of Ophthalmology, 2001, 1023-1031, 108(6).
Brandt, James, PA022 Phase III, 3-month Comparison in Timolol with AGN-192024: A New Ocular Hypotensive Lipid for Glaucoma Management, Presented at 2000 Am. Acad. Ophthalmology, Ann. Mtg., Oct. 23, 2000, 1 Page.
Brubaker, Richard et al, Effects of AGN 192024, a new Ocular Hypotensive Agent, on Aqueous Dynamics, American journal of Ophthalmology, 2001, 19-24, 131(1).
Brundy, Gordon, Synthesis of 17-Phenyl-18, 19, 20-Trinorprostaglandins I. The PG1 Series, Prostaglandins, 1975, 1-4, 9(1).
Business Wire, Phase III Lumigan, AGN-192024- Data Presented At American Academy of Ophthalmology, American Academy of Ophthalmology, 2000, 1-3, Retrieved Dec. 14, 2010.
Cadet, Patrick et al, Molecular Identification and Functional Expression of µ3, a Novel Alternatively Spliced Variant of the Human µ Opiate Receptor Gene, J. Immunol., 2003, 5118-5123, 170.
Camras, Carl B. et al, Bimatoprost, the Prodrug of a Prostaglandin Analogue, Br J Ophthalmol, 2008, 862-863, 92.
Camras, Carl B. et al, Comparison of Latanoprost and Timolol in Patients with Ocular Hypertension and Glaucoma, Ophthalmology, 1996, 138-147, 103(1).
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg.
Camras, Carl B. et al, Latanoprost, a prostaglandin Analog, for Glaucoma Therapy, Ophthalmology, 1996, 1916-1924, 103(11).
Camras, Carl B. et al, Multiple Dosing of Prostaglandin F2α or Epinephrine on Cynomolgus Monkey Eyes, Investigative Ophthalmology & Visual Science, Sep. 1988, 1428-1436, 29(9).
Camras, Carl B. et al, Multiple Dosing of Prostaglandin F2α or Epinephrine on Cynomolgus Monkey Eyes, Investigative Ophthalmology & Visual Science, 1987, 463-469, 28(3).
Camras, Carl B. et al, Multiple Dosing of Prostaglandin F2α or Epinephrine on Cynomolgus Monkey Eyes, Investigative Ophthalmology & Visual Science, 1987, 921-926, 28(6).
Camras, Carl B. et al, Reduction of Intraocular Pressure in Normal and Glaucomatous Primate (*Aotus trivirgatus*) Eyes by Topically Applied Prostaglandin F2α, Current Eye Research, 1981, 205-209, 1 (4).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
CAS RN 155206-00-1 May 20, 1994.
Cayatte, Antonio et al, The Thromboxane A2 Receptor Antagonist, S18886, Decreases atherosclerotic Lesions and serum Intracellular Adhesion Molecule-1 in the Apo E Knockout Mouse, 71st Scientific Sessions, 1998, I-115 (Abstract), 98(17).
Chen, June et al, AGN 191129: A Neutral Prostaglandin F2n (PGF2n) Analog That Lacks the Mitogenic and Uterotonic Effects Typical of FP Receptor Agonists, Glaucoma, Anatomy & Pathology, Physiology & Pharmacology, 1999, 3562-B420, 40(4).
Chen, June et al, Replacement of the Carboxylic Acid Group of Prostaglandin F2α (PGF2α) with Certain Non-Ionizable Substituents Results in Pharmacologically Unique Ocular Hypotensive Agents, 11th Intl Conf. Advances Prostaglandin & Leukotriene Res.: Basic Sci. & New Clinical Applications—Abstract Book, 2000, 1 page.
Chen, June et al, Studies on the Pharmacology of Prostamide F2α, A Naturally Occurring Substance, Brit. J. Pharmacology, 2001, 63P, 133.
Chyun, Yong et al, Stimulation of Bone Formation by Prostaglandin E2, Prostaglandins, 1984, 97-103, 27(1).
Clissold, D., The Potential for Prostaglandin Pharmaceuticals, Lipids in Health and Nutrition, 1999, 115-129, 244, The Royal Society of Chemistry.
Cohen, Joel, Enhancing the Growth of Natural Eyelashes: The Mechanism of Bimatoprost-Induced Eyelash Growth, Dermatol Surg, 2010, 1361-1371, 36(9).
Coleman, Robert et al, Prostanoids and Their Receptors, Comprehensive Medicinal Chemistry, 1990, 643-714, 3.
Coleman, Robert, VIII. International union of Pharmacology Classification of Prostanoid Receptors: Properties, Distribution, and Structure of the Receptors and Their Subtypes, The American Society for Pharmacology and Experimental Therapeutics, 1994, 205-229, 26(2).
Collins, Paul et al, Synthesis of Therapeutically Useful Prostaglandin and Prostacyclin Analogs, Chem. Rev., 1993, 1533-1564, 93.
Corsini, A. et al, (5Z)-Carbacyclin Discriminates Between Prostacyclin-Receptors Coupled to Adenylate Cyclase in Vascular Smooth Muscle and Platelets, Br. J. Pharmac., 1987, 255-261, 90.
Cowley, Lorraine et al, How Women Receiving Adjuvant Chemotherapy For Breast Cancer Cope With Their Treatment: a Risk Management Perspective, Journal of Advanced Nursing, 2000, 314-321, 31(2).
Cox, Colin et al, Protein Fabrication Automation, Protein Science, 2007, 379-390, 16.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Darnell, J., Cell-to-Cell Signaling: Hormones and Receptors, Molecular Cell Biology, 1990, 738-743, vol. 82, Darnell, J., Lidish, H., Baltimore, D., Eds., New York, New York.
Davies, Sean, Hydrolysis of Bimatoprost (Lumigan) to Its Free Acid By Ocular Tissue In Vitro, Journal of Ocular Pharmacology and Therapeutics, 2003, 45-54, 19(1).
De Asua, L Jimenez et al, The Stimulation of the Initiation of DNA Synthesis and Cell Division in Swiss Mouse 3T3 Cells by Prostaglandin F2α Requires Specific Functional Groups in the Molecule, J. Biol. Chemistry, 1983, 8774-8780, 256(14).
Dean, T.R. et al, Improvement of Optic Nerve Head Blood Flow After One-Week Topical Treatment with Travoprost (AL06221) in the Rabbit, Investigative Ophthalmology & Visual Science, Mar. 15, 1999, 2688-B563, 40(4).
Del Toro, F. et al, Characterization of Prostaglandin E2 Receptors and Their Role in 24,25-(OH)2D3-Mediated Effects on Resting Zone Chondrocytes, Journal of Cellular Physiology, 2000, 196-208, 182.
Delong, Mitchell, Prostaglandin Receptor Ligands: Recent Patent Activity, IDrugs, 2000, 196-208, 3(9).
Depperman, William, Up-To-Date Scalp Tonic, Book Reviews, 1970, 1115, 283(20).
Dirks, Monte et al, Efficacy and Safety of the Ocular Hypotensive Lipid™ 192024 in Patients with Elevated IOP: A 30-Day Comparison with Latanoprost, Investigative Ophthalmology & Visual Science, Mar. 15, 2000, S514, 41(4).
Dubiner, Harvey, Efficacy and Safety of Bimatoprost in Patients With Elevated Intraocular Pressure: a 30-Day Comparison With Latanoprost, Surv, Ophthalmol, 2001, S353-S560, 45 (4).
Easthope, Stephanie et al, Topical Bimatoprost, Drug Aging, 2002, 231-248, 19(3).
Eisenberg, Dan et al, A Preliminary Risk-Benefit Assessment of Latanoprost and Unoprostone in Open-Angle Glaucoma and Ocular Hypertension, Drug Safety, 1999, 505-514, 20(6).
Ellis, Cathy et al, Metabolism of Prostaglandin D2 in the Monkey*, The Journal of Biological Chemistry, 1979, 4152-4163, 254(10).
Enyedi, Laura et al, The Effectiveness of Latanoprost for the Treatment of Pediatric Glaucoma, J AAPOS, 1999, 33-39, 3(1).

(56) References Cited

OTHER PUBLICATIONS

Fagien, Steven, Management of Hypotrichosis of the Eyelashes: Focus on Bimatoprost, Clinical, Cosmetic and Investigational Dermatology, 2010, 39-48, 3.
Fagot, Dominique et al, Mitogenic Signaling by Prostaglandins in Chemically Transformed Mouse Fibroblasts: Comparison with Phorbol Esters and Insulin, Endocrinology, 1993, 1729-1734, 132(4).
Fall, P.M., Inhibition of Collagen Synthesis by Prostaglandins in the Immortalized Rat Ostroblastic Cell Line Pyla: Structure-Activity Relations and Signals Transduction Mechanisms, J. Bone Miner Res., 1994, 1935-1943, 9(12).
Faulkner, Robert, Aqueous Humor Concentrations of Bimatoprost Free Acid, Bimatoprost and Travoprost Free Acid in Cataract Surgical Patients administered Multiple Topical Ocular Doses of LUMIGAN or TRAVATAN, Journal of Ocular Pharmacology and Therapeutics, 2010, 147-156, 26(2).
FDA Approves Two New intraocular Pressure Lowering Drugs for the Management of Glaucoma, Mar. 16, 2001, FDA News.
FDA Label for Approved NDA 22-184 of Lumigan 0.01% and Lumigan 0.03%, Aug. 31, 2010.
Fiscella, Richard, Peek into the Drug Pipeline, Review of Optometry Online, Jan. 15, 2001, 5 pages.
Fitzpatrick, F.A., Separation of Prostaglandins and Thromboxanes by Gas Chromatography with Glass Capillary Columns, Analytical Chemistry, 1978, 47-52, 50(1).
Flisiak, Robert et al, Effect of Misoprostol on the Course of Viral Hepatitis B, Hepato-Gastroenterology, 1997, 1419-1425, 44.
Freedman, Tovia et al, Social and Cultural Dimensions of Hair Loss in Women Treated for Breast Cancer, Cancer Nursing, 1994, 334-341, 17(4).
Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Funk, Colin et al, Cloning and Expression of a cDNA for the Human Prostaglandin E Receptor EP1 Subtype*, The Journal of Biological Chemistry, Dec. 15, 1993, 26767-26772, 268(35).
Gandolfi, Stefano, Three-month Comparison of Bimatoprost and Latanoprost in Patients With Glaucoma and Ocular Hypertension, Adv. Ther, 2001, 110-121, 18.
Garadi, R et al, Travoprost: A New Once-Daily Dosed Prostaglandin For The Reduction of Elevated Intraocular Pressure, Investigative Ophthalmology & Visual Science, 1999, 4378-B181, Abstract.
Geng, Ling et al, Misoprostol, A PGE1 Analog That is Radioprotective For Murine Intestine and Hair, Induces Widely Different Cytokinetic Changes in These Tissues, The Journal of Investigative Dermatology, 1996, 858, 106(4).
Geng, Ling et al, Topical or Systemic 16,16 dm Prostaglandin E2 or WR-2721 (WR-1065) Protects Mice From Alopecia After Fractionated Irradiation, Int. J. Radiat. Biol., 1992, 533-537, 61(4).
Gerth, Jeff et al, Drug Makers Reap Profits on Tax-Backed Research, Apr. 23, 2000, 10 pages, New York Times.
Giuffre, Giuseppe, The Effects of Prostaglandin F2α in the Human Eye, Graefe's Archive Clin. & Exper. Ophthal., 1985, 139-141, 222.
Griffin, Brenda et al, AL-8810: A Novel Prostaglandin F2α Analog with Selective Antagonist Effects at the Prostaglandin F2α (FP) Receptor, Journal of Pharmacology and Experimental Therapeutics, 1999, 1278-1284, 290(3).
Grow (Verb) Definition, Merriam Webster's Dictionary, Retrieved from http://www.merriam-webster.com/dictionary/growing on Jul. 9, 2012.
Hall, Alistair et al, Clinprost Tijin, Current Opinion in Cardiovascular, Pulmonary & Renal Investigational Drugs, 1999, 605-610, 1(5).
Hallinan, Ann et al, Aminoacetyl Moiety as a Potential Surrogate for Diacylhydrazine Group of SC-51089, a Potent PGE2 Antagonist, and Its Analogs, J Med Chem, 1996, 609-613, 39.
Hanson, W R et al, 16,16 dm Prostaglandin2 Protects From Acute Radiation-Induced Alopecia in Mice, Clinical Research, 1988, 906A, 36(6).
Hanson, W R et al, Subcutaneous or Topical Administration of 16,16 Dimethyl Prostaglandin E2 Protects From Radiation-Induced Alopecia in Mice, Int. J. Radiation Oncology Biol. Phys., 1992, 333-337, 23.
Hartke, J.R. et al, Prostanoid FP Agonists Build Bone in the Ovariectomized Rat, Prostanoid FP Agonists Build Bone in the Ovariectomized Rat, 1999, S207.
Hayashi, Masaki et al, Prostaglandin Analogues Possessing Antinidatory Effects. 1. Modification of the ω Chain, J. Med. Chem., 1980, 519-524, 23.
Hecker, Markus et al, Studies on the Interaction of Minoxidil with Prostacyclin Synthase in Vitro, Biochemical Pharmacology, 1988, 3363-3365, 37(17).
Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).
Higginbotham, Eve et al, One-Year, Randomized Study Comparing Bimatoprost And Timolol In Glaucoma And Ocular Hypertension, Archives Of Opthalmology, Oct. 2002, 1286-1293, 120 (10), US.
Houssay, Alerto, Effects of Prostaglandins Upon Hair Growth in Mice, Acta Physiol. Latinoam., 1976, 186-191, 26.
Huang, a. et al, Different Modes of Inhibition of Increase in Cytosolic Calcium and Aggregation of Rabbit Platelets by Two Thromboxane A2 Antagonists, Asia Pacific Journal of Pharmacology, 1994, 163-171, 9.
Hulan, H.W. et al, The Development of Dermal Lesions and Alopecia in Male Rats Fed Rapeseed Oil, Canadian Journal of Physiology and Pharmacology, 1976, 1-6, 54(1).
Hulan, H.W. et al, The Effect of Long-Chain Monoenes on Prostaglandin E2 Synthesis by Rat Skin, Lipids, 1977, 604-609, 12(7).
Hunt, Nigel et al, The Psychological Impact of Alopecia, BMJ, Oct. 2005, 951-953, 331.
Ichikawa, A. et al, Molecular Aspects of the Structures and Functions of the Prostaglandin E Receptors, J. Lipid Mediators Cell Signalling, 1996, 83-87, 14.
Informa UK Ltd., AGN-192024, 2006, 3 Pages.
Inoue, Hironishi, Thromboxane A2 receptor antagonists, Oct. 1996, 1221-1225, 32(10), Pharmaceutical Society of Japan.
J Am Pharm Assoc-, Agents for Glaucoma, New Drugs of 2001, 2001, 4 pages, 42(2), Journal of the American Pharmaceutical Association, http://www.edscape.com/viewarticle/436631_22, US.
Jakobsson, Per-Johan et al, Membrane-Associated Proteins in Eicosanoid and Glutathione Metabolism (MAPEG), American Journal of Respiratory and Critical Care Medicine, 2000, S20-S24, 161.
Jimenez, J.J. et al, Stimulated Monocyte-Conditioned Media Protect From Cytosine Arabinoside-Induced Alopecia in Rat, Friday Afternoon Subspecialty Meetings, 1990, 973A.
Johnstone, M.A., Brief Latanoprost RX Induces Hypertrichosis, Glaucoma Clinical Pharmacology II Poster Presentation, 1998, S258, 39(4).
Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).
Jordan, B.A. et al, G-Protein-Coupled Receptor Heterodimerization Modulates Receptor Function, Nature, Jun. 17, 1999, 697-700, 399(6737).
Karim, S.M. et al, Prostaglandins and Human Respiratory Tract Smooth Muscle: Structure Activity Relationship, Advances in Prostaglandin and Thromboxane Research, 1980, 969-980, 7.
Karuss, Achim et al, Evidence for Human Thromboxane Receptor Heterogeneity Using a Novel Series of 9,11-Cyclic Carbonate Derivatives of Prostaglandin F2α, British Journal of Pharmacology, 1996, 1171-1180, 117.
Katz, L.J. et al, Comparison of Human Ocular Distribution of Bimatoprost and Latanoprost, 2010, P450.
Kaufman, Paul, Effects of Intracamerally Infused Prostaglandins on Outflow Facility in Cynomolgus Monkey Eyes with Intact or Retrodisplaced Ciliary Muscle, Experimental Eye Research, 1986, 819-827, 43.

(56) References Cited

OTHER PUBLICATIONS

Kende, Andrew et al, Prostaglandin Phosphonic Acids Through Homolytic Halodecarboxylation of Prostaglandins F1α and F2α, Tetrahedron Letters, 1999, 8189-8192, 40.
Kerstetter, J.R. et al, Prostaglandin F2α-1-Isopropylester Lowers Intraocular Pressure Without Decreasing Aqueous Humor Flow, American Journal of Ophthalmology, 1988, 30-34, 105.
Kiriyama, Michitaka et al, Ligand Binding Specificities of the Eight Types and Subtypes of the Mouse Prostanoid Receptors Expressed in Chinese Hamster Ovary Cells, British Journal of Pharmacology, 1997, 217-224, 122.
Kluender, Harold et al, The Synthesis of Dimethylphosphonoprostaglandin Analogs, Prostaglandins and Medicine, 1979, 441-444, 2.
Kvedar, Joseph et al, Topical Minoxidil in the Treatment of Male Pattern Alopecia, Pharmacotherapy, 1987, 191-197, 7(6).
Lachgar, S. et al, Effect of VEGF and Minoxidil on the Production of Arachidonic Acid Metabolites by Cultured Hair, Dermal Papilla Cells, Eur. J. Dermatol, 1996, 365-368, 6.
Lachgar, S. et al, Hair Dermal Papilla Cell Metabolism is Influenced by Minoxidil, Fundamental & Clinical Pharmacology, 1997, 178, 11(2).
Lachgar, S. et al, Modulation by Minoxidil and VEGF of the Production of Inflammatory Mediators by Hair Follicle Dermal Papilla Cells, Groupe de Rocherche Dermatologique, 1995, 161, 104(1).
Lambert, Joseph, Clinical Study Report, A Multicenter, Double-Masked, Randomized, Parallel, 3-Month study (with Treatment Extended to 1 year) of the Safety and Efficacy of AGN 192024 0.03% Ophthalmic Solution Administered Once-Daily or Twice-daily Compared with Timolol 0.5% Ophthalmic Solution Administered Twice-Daily in Subjects with Glaucoma or Ocular Hypertension, Study No. 192024-009, Phase 3, 1998, 34 pages.
Lardy, C. et al, Antiaggregant and Antivasospastic Properties of the New Thromboxane A2 Receptor Antagonist Sodium 4-[[1-[[[(4 Chlorophenyl)sulfony]amino]methyl]cyclopentyl]methyl] benzeneacetate, Arzneim.-Forsch./Drug Res., 1994, 1196-1202, 44(11).
Law, Simon, Bimatoprost in the Treatment of Eyelash Hypotrichosis, Clinical Ophthalmology, 2010, 349-358, 4.
Lee, Ping-Yu et al, The Effect of Prostaglandin F2α on Intraocular Pressure in Mormotensive Human Subjects, Investigative Ophthalmology & Visual Science, Oct. 1988, 1474-1477, 29(10).
Lee, Vincent et al, Improved Ocular Drug Delivery with Prodrugs, Prodrugs: Topical and Ocular Drug Delivery, 1992, 221-297, Kenneth Sloan Edition.
Lemieux, Julie et al, Chemotherapy-Induced Alopecia and Effects on Quality of Life Among Women With Breast Cancer: a Literature Review, Psycho-Oncology, 2008, 317-328, 17.
Liang, Y. et al, Identification and Pharmacological Characterization of the Prostaglandin FP Receptor and FP Receptor Variant Complexes, Br. J. Pharmacol., 2008, 1079-1093, 154.
Liljebris, Charlotta et al, Derivatives of 17-Phenyl-18,19,20-trinorprostaglandin F2α Isopropyl Ester: Potential Antiglaucoma Agents, J. Med. Chem., 1995, 289-304, 38.
Ling, Geng et al, 16,16 dm Prostaglandin E2 Protects Mice From Fractionated Radiation-Induced Alopecia, Clinical Research, 1990, 858A, 38(3).
Lumigan 6-Month Phase 3 Data Presented at American Glaucoma Society Meeting, Mar. 2, 2001, 4 pages, Business Wire.
Lumigan Package Insert, Mar. 2001, 6 pages, NDA 21-275.
Lundy, M.W. et al, Restoration of Cancellous Architecture and Increased Bone Strength in Aged Osteopenic Rats Treated with Fluprostenol, 21st Annual Meeting of the American Society for Bone and Mineral Research, 1999, S401.
Luoma, Minna-Liisa et al, The Meaning of Quality of Life in Patients Being Treated For Advanced Breast Cancer: a Qualitative Study, Psycho-Oncology, 2004, 729-739, 13.
Maddox, Yvonne et al, Amide and I-amino Derivatives of F Prostaglandins as Prostaglandin Antagonists, Nature, Jun. 15, 1978, 549-552, 273.

Malkinson, Frederick et al, Prostaglandins Protect Against Murine Hair Injury Produced by Ionizing Radiation of Doxorubicin, J. Invest Dermatol., 1993, 135S-137S, 101.
Mansberger, Steven et al, Eyelash Formation Secondary to Latanoprost Treatment in a Patient With Alopecia, Arch. Opthalmol., 2000, 718-719, 118.
Maruyama, Takayuki et al, EP1 Receptor Antagonists Suppress Tactile Allodynia in Rats, Prostaglandins & Other Lipid Mediators, 1999, 217(Abstract), 59.
Matsumura, H. et al, Brain and Neuroscience, 1998, 79-89.
Maw, Graham, Chapter 8. Pharmacological Therapy for the Treatment of Erectile Dysfunction, Annual Reports in Medicinal Chemistry, 1999, 71-80.
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
McCullough, Peter et al, Ridogrel Janssen, Current Opinion in Anti-inflammatory & Immunodulatory Investigational Drugs, 1999, 265-276, 1(3).
McMurry, John, Amides, Organic Chemistry, 1984, 794.
Medical Review, Application No. 21-275, Center for Drug Evaluation and Research, 2001.
Medline, Bimatoprost (Ophthalmic), Bimatoprost, Jul. 24, 2001, 4 pages, Medlineplus. Health Information, Online.
Michelet, Jean-Francois et al, Activation of Cytoprotective Prostaglandin Synthase-1 by Minoxidil as a Possible Explanation for Its Hair Growth-Stimulating Effect, J. Invest. Dermatol., 1997, 205-209, 108.
Mihele, Densia et al, Cercetarea Actiunii Hepatoprotectoare A Unor Prostaglandine De Sinteza, Farmacia, 1999, 43-58, 67(5).
Millikan, Larry, Treatment of Alopecia, The Journal of Clinical Pharmacology, 1987, 715, 27(8).
Millikan, Larry, Treatment of Male Pattern Baldness, Drug Therapy, 1989, 62-73.
Mishima, Hiromu, A Comparison of Latanoprost and Timolol in Primary Open-Angle Glaucoma and Ocular Hypertension, Arch. Opthalmol., 1996, 929-932, 114.
Miyamoto, Terumasa et al, A Comparison in the Efficacy and Safety Between Ramatroban (BAY u 3405) and Ozagrel-HCl for Bronchial Asthma—A Phase III, Multi-Center, Randomized, Double-Blind, Group Comparative Study, 1997, 599-639.
Mori, S. et al, Effects of Prostaglandin E2 on Production of New Cancellous Bone in the Axial Skeleton of Ovariectomized Rats, Bone, 1990, 103-113, 11.
Morris, Carrie et al, The Role of Bimatoprost Eyelash Gel in Chemotherapy-Induced Madarosis: An Analysis of Efficacy and Safety, Int. J. Trichology, 2011, 84-91, 3(2).
Moses, Robert, Adler's Physiology of the Eye, 1970, 1-18, 5th Ed.
Murakami, T. et al, Effect of Isocarbacyclin Methyl Ester Incorporated in Lipid Microspheres on Experimental Models of Peripheral Obstructive Disease, Drug Res., 1995, 991-994, 45(9).
Narumiya, Shuh et al, Roles of Prostanoids in Health and Disease; Lessons From Receptor-Knockout Mice, Common Disease: Genetic and Pathogenetic Aspects of Multifactorial Diseases, 1999, 261-269.
Neau, Steven, Pharmaceutical Salts, Water-Insoluble Drug Formulation, 2008, 417-435.
Negishi, Manabu et al, Molecular Mechanisms of Diverse Actions of Prostanoid Receptors, Biochimica et Biophysica Acta, 1995, 109-120, 1259.
New Drugs for Glaucoma, FDA Consumer Magazine, May-Jun. 2001.
Norrdin, R.W. et al, The Role of Prostaglandins in Bone in Vivo, Prostaglandins Leukotrienes and Essential Fatty Acids, 1990, 139-149, 41.
Ochoa, Blanca, Instilled Bimatoprost Ophthalmic Solution in Patients with Eyelash Alopecia Areata, Letters, Sep. 1, 2009, 530-532, 61(3), J. Am. Acad. Dermatol.
Olsen, Elise et al, Transdermal Viprostol in the Treatment of Male Pattern Baldness, J. Am. Acad. Dermatol., 1990, 470-472, 23.
Orlicky, D.J., Negative Regulatory Activity of a Prostaglandin F2α Receptor Associated Protein (FPRP), Prostaglandins, Leukotrienes and Essential Fatty Acids, 1996, 247-259, 54(4).

(56) References Cited

OTHER PUBLICATIONS

Ortonne, Jean-Paul et al, Hair Melanin's Hair Color: Ultrastructural and Biochemical Aspects, Journal of the Society for Investigative Dermatology, 1993, 82S-89S.
Paragraph IV Letter, Jul. 26, 2010.
Pfeiffer, N, New Developments in Glaucoma Drug Therapy, Ophthalmologist, 1992, W1-W13, 89.
Pharmaprojects No. 6321, 2006, 1 page.
Phase 3 Lumigan—AGN 192024—Data Presented At American Academy of Ophthalmology, Allergan Press Release, Mar. 1, 2000.
Physicians' Desk Reference, 56th ed., pp. 212-13, 543, 553-54, 2864-65 (2002).
Poyer, J.F. et al, Prostaglandin F2α Effects on Isolated Rhesus Monkey Ciliary Muscle, Invest. Ophthalmol. Vis. Sci., Nov. 1995, 2461-2465, 36(12).
Preparation of '404 Patent Documents for European Patent Office; Defendant Athena Cosmetics, Inc., Supplemental Invalidity Contentions Pursuant to Patent Local Rule 3-3, 2009.
Preparation of '404 Patent Documents for European Patent Office; Defendant Peter Thomas Roth Labs LLC and Peter Thomas Roth, Inc.'s Invalidity Contentions Pursuant to Patent Local Rule 3-3, 2009.
Preparation of '404 Patent Documents for European Patent Office; Defendants Metrics LLC, Product Innovations LLC; Stella International LLC; and Nutra-Luxe, M.D. LLC's; Local Patent Rule 3-3 Preliminary Invalidity Contentions, 2009.
Preparation of '404 Patent Documents for European Patent Office; Invalidity Contentions Pursuant to Patent Local Rule 3-3, 2008.
Pucci, Neri et al, Long Eyelashes in a Case Series of 93 Children With Vernal Keratoconjunctivitis, Pediatrics, 2005, e86-e91, 115.
Rampton, D.S. et al, Anti-inflammatory Profile in Vitro of Ridogrel, A Putative New Treatment for Inflammatory Bowel Disease, Immunology, Microbiology, and Inflammatory Disorders, 1999, G3477.
Resul, B et al, Phenyl-substituted Prostaglandins: Potent and Selective Antiglaucoma Agents, J. Med. Chem., Jan. 22, 1993, 243-248, 36(2).
Reynolds, A, Darkening of Eyelashes in a Patient Treated With Latanoprost, Eye, 1998, 741-743, 12.
Richer, Marie-Claire et al, Living In It, Living With It, And Moving On: Dimensions of Meaning During Chemotherapy, 2002, 113-119, 29(1).
Rigaudy, J. et al, Nomenclature of Organic Chemistry Sections A, B. C, D, E, F, and H, InCL Union of Pure & Applied Chemistry, Organic Chemistry Div., Comm'n. On Nomenclature of Organic Chemistry, 1979, 255-256.
Roenigk, Henry, New Topical Agents for Hair Growth, Clinics in Dermatology, 1988, 119-121, 6(4).
Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).
Roof, S.L. et al, mRNA Expression of Prostaglandin Receptors EP1, EP2, EP3 and EP4 in Human Osteoblast-Like Cells and 23 Human Tissues, 18 Annual Meeting of the American Society for Bone and Mineral Research, 1996, S337.
Roseborough, Ingrid et al, Lack of Efficacy of Topical Latanoprost and Bimatoprost Ophthalmic Solutions in Promoting Eyelash Growth in Patients with Alopecia Areata, J Am Acad Dermtol, Apr. 2009, 705-706, 60(4).
Ruel, Rejean et al, New Class of Biphenylene Dibenzazocinones as Potent Ligands for the Human EP1 Prostanoid Receptor, Bioorganic & Medicinal Chemistry Letters, 1999, 2699-2704, 9.
Sakuma, Yoko et al, Crucial Involvement of the EP4 Subtype of Prostaglandin E Receptor in Osteoclast Formation by Proinflammatory Cytokines and Lipopolysacharide, Journal of Bone and Mineral Research, 2000, 218-227, 15(2).
Sauk, John et al, Influence of Prostaglandins E1, E2, and Arachidonate on Melanosomes in Melanocytes and Keratinocytes of Anagen Hair Bulbs in Vitro, The Journal of Investigative Dermatology, 1975, 332-337, 64.

Shaikh, M.Y. et al, Hypertrichosis of the Eyelashes From Prostaglandin Analog Use: a Blessing or a Bother to the Patient?, Journal of Ocular Pharmacology and Therapeutics, 2006, 76-77, 22(1).
Sharif, N.A. et al, [3H]AL-5848 ([3H]9(β-(+)-Fluprostenol). Carboxylic Acid of Travoprost (AL-6221), a Novel FP Prostaglandin o Study the Pharmacology and Autoradiographic Localization of the FP Receptor, J. Pharm. Pharmacol., 1999, 685-694, 51.
Sharif, N.A. et al, Cat Iris Sphincter Smooth-Muscle Contraction: Comparison of FP-Class Prostaglandin Analog Agonist Activities, J. Ocul. Pharmacol. Ther, Apr. 2008, 152-163, 24(2).
Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther, 2003, 437-455, 19.
Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.
Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).
Sharif, N.A. et al, Update and Commentary on the Pro-Drug Bimatoprost and a Putative Prostamide Receptor, Expert Rev. Ophthalmol., 2009, 477-489, 4(5).
Sharif, Najam, Bimatoprost and Its Free Acid Are Prostaglandin FP Receptor Agonists, European Journal of Pharmacology, 2001, 211-213, 432.
Sherwood, Mark et al, Six-Month Comparison of Bimatoprost Once-Daily and Twice-Daily with Timolol Twice-Daily in Patients with Elevated Intraocular Pressure, Survey of Ophthalmology, 2001, S361-S368, 45(4).
Shih, Mei-Shu et al, PGE2 Induces Regional Remodeling Changes in Haversian Envelope: a Histomorphometric Study of Fractured Ribs in Beagles, Bone and Mineral, 1986, 227-264, 1.
Shimazaki, Atsushi et al, Effects of the New Ethacrynic Acid Derivative SA9000 on Intraocular Pressure in Cats and Monkeys, Biol. Pharm. Bull., 2004, 1019-1024, 27(7).
Shimazaki, Atsushi et al, New Ethacrynic Acid Derivatives as Potent Cytoskeletal Modulators in Trabecular Meshwork Cells, Bio. Pharm. Bull., 2004, 846-850, 27(6).
Sjoquist, Birgitta et al, Ocular and Systemic Pharmacokinetics of Latanoprost in Humans, Surv. Ophthalmol., Aug. 2002, S6-S12, 47(Suppl 1).
Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.
Sorbera, L.A. et al, Travoprost, Drugs of the Future, 2000, 41-45, 25(1).
Souillac, Pierre et al, Characterization of Delivery Systems, Differential Scanning Calorimetry, 1999, 212-227, 49.
Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).
Sredni, Benjamin et al, The Protective Role of the Immunomodulator AS101 Against Chemotherapy-Induced Alopecia Studies on Human and Animal Models, Int. J. Cancer, 1996, 97-103, 65.
Stahl, Heinrich et al, Chapter 12: Monographs on Acids and Bases, Handbook of Pharmaceutical Salts, 2008, 265-327.
Stamer, W.D. et al, Cellular Basis for Bimatoprost Effects on Human Conventional Outflow, Invest. Ophthalmol. Vis. Sci., Oct. 2010, 5176-5181, 51(10).
Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).
Stjernschantz, Johan et al, Phenyl Substituted Prostaglandin Analogs for Glaucoma Treatment, Phenyl Substituted Prostaglandin Analogs for Glaucoma Treatment, 1992, 691-704, 17(8).

(56) References Cited

OTHER PUBLICATIONS

Stjernschantz, Johan et al, Studies on Ocular Inflammation and Development of a Prostaglandin Analogue for Glaucoma Treatment, Exp. Eye Res., Apr. 2004, 759-766, 78(4).
Supplement A (Lumigan®), Physician's Desk Reference 2001, Mar. 2001.
Swarbrick, James et al, Salt Forms of Drugs and Absorption, Encyclopedia of Pharmaceutical Technology, 1988, 453-499, 13.
Terada, Nobuhisa et al, Effect of a Thromboxane A2 Receptor Antagonist Ramatroban (BAY u 3405), on Inflammatory Cells, Chemical Mediators and Non-Specific Nasal Hyperreactivity After Allergen Challenge in Patients with Perennial Allergic Rhinitis, Allergoloy International, 1998, 59-67, 47.
The Newsletter of Glaucoma Foundation, 2000, 11 pages, 11(2).
Tomita, Yasushi et al, Melanocyte-Stimulating Properties of Arachidonic Acid Metabolites: Possible Role in Postinflammatory Pigmentation, Pigment Cell Research, 1992, 357-361, 5.
Tosti, Antonella et al, Drug-Induced Hair Loss and Hair Growth: Incidence, Management and Avoidance, Drug Safety, 1994, 310-317, 10(4).
Tosti, Antonella et al, Hypertrichosis of the Eyelashes Caused by Bimatoprost, J Am Acad Dermatol, Nov. 2004, S149-S150, 51(5).
Travatan (travoprost ophthalmic solution) 0.004% Product Insert, NDA 21-257, Mar. 16, 2001, 7 Pages.
Trueb, Ralph, Chemotherapy-Induced Alopecia, Semin Cutan Med Surg, 2009, 11-14, 28.
U.S. Appl. No. 11/805,122, Resp. to Office Action dated Jan. 21, 2009.
Ueda, Ken et al, Cortical Hyperostosis Following Long-Term Administration of Prostaglandin E1 in Infants with Cyanotic Congenital Heart Disease, Journal of Pediatrics, 1980, 834-836, 97(5).
Ulrich, Jens et al, Skin Toxicity of Anti-Cancer Therapy, J Dtsch Dermatol Ges., 2008, 959-975, 6.
Van Alphen, G.W.H.M. et al, The effect of Prostaglandins on the Isolated Internal Muscles of the Mammalian Eye, Including Man, Documenta Ophthalmologica, 1977, 397-415, 42(4).
Vandenburg, A.M. et al, A One-Month Dose Response Study of AGN 192024, A Novel Antiglaucoma Agent, in Patients with Elevated Intraocular Pressure, Glaucoma Clinical Pharmacology IV Poster Presentation, 1999, S830, 40 (4).
Vandenburgh, Amanda, reply to Alan L. Robin, An Accurate Comparison of Bimatoprost's Efficacy and Adverse Effects, Arch Ophthalmol, Jul. 2002, 997-1000, 120.
Vayssairat, Michael, Preventive Effect of an Oral prostacyclin Analog, Beraprost Sodium, on Digital Necrosis in Systemic Sclerosis, J. Rheumatol, 1999, 2173-2178, 26.
Vengerovsky, A.I. et al, Hepatoprotective action of prostaglandins, Experimental and Clinical Pharmacology, 1997, 78-82, 60(5).
Verbeuren, T. et al, The TP-Receptor Antagonist S 18886 Unmasks Vascular Relaxation and Potentiates the Anti-Platelet Action of PGD2, New Antithrombotic Agents, Jun. 11, 1997, 693.
Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).
Villumsen, J. et al, Prostaglandin F2α-isopropylester Eye Drops: Effect on Intraocular Pressure in Open-Angle Glaucoma, Br. J. Ophthalmol., 1989, 975-979, 73.
Vincent, J.E. et al, Letter to the Editor Prostaglandin Synthesis and Selenium Deficiency a Hypothesis, Prostaglandins, 1974, 339-340, 8(4).
Vippagunta, Sudha et al, Crystalline Solids, Advanced Drug Delivery Reviews, 2001, 3-26, 48.
Voss, N.G. et al, Induction of Anagen Hair Growth in Telogen Mouse Skin by Topical Latanoprost Application, Glaucoma Pharmacology, Cellular, Mechanism II, Mar. 15, 1999, S676, 40(4).
Waddell, K.A. et al, Combined Capillary Column Gas Chromatography Negative Ion Chemical Ionization Mass Spectrometry of Prostanoids, Biomedical Mass Spectrometry, 1983, 83-88, 10(2).
Wand, Martin, Latanoprost and Hyperpigmentation of Eyelashes, Arch Ophthalmology, Sep. 1997, 1206-1208, 115.
Wang, Yili et al, Design and Synthesis of 13,14-Dihydro Prostaglandin F1α Analogues as Potent and Selective Ligands for the Human FP Receptor, J. Med. Chem., 2000, 945-952, 43.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Whitcup, Clinical Study Report, A Multi-Center, Investigator-Marked, Randomized, Parallel Study of the Safety and Efficacy of AGN 192024 0.03% Ophthalmic Solution Compared with Latanoprost 0.005% Ophthalmic Solution Administered Once-Daily in Subjects with Glaucoma or Ocular Hypertension, Study No. 192024-010-01, Phase 3b, 1999, 1, Allergan.
White, J.H. et al, Heterodimerization is Required for the Formation of a Functional GABA(B) Receptor, Nature, Dec. 17, 1998, 679-682, 396(6712).
Whitson, Jess, Travoprost—a New Prostaglandin Analogue for the Treatment of Glaucoma, Expert Opin. Pharmacother, 2002, 965-977, 3 (7).
Williams, Jane et al, A Narrative Study of Chemotherapy-Induced Alopecia, 1999, 1463-1468, 26(9).
Willis, Anthony, Prostaglandins and Related Lipids, vol. I, Chemical and Biochemical Aspects, CRC Handbook of Eicosanoids, 1987, 80-97, 1.
Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).
Woodward, David et al, Bimatoprost Effects on Aqueous Humor Dynamics in Monkeys, J. Ophthalmol., 2010, 1-5, vol. 2010.
Woodward, David et al, Bimatoprost: a Novel Antiglaucoma Agent, Cardiovascular Drug Reviews, 2004, 103-120, 22(2).
Woodward, David et al, Emerging Evidence for Additional Prostanoid Receptor Subtypes, Current Topics in Pharmacology, 1998, 153-162, 4.
Woodward, David et al, Identification of an antagonist that selectively blocks the activity of prostamides (prostaglandin-ethanolamides) in the feline iris, British Journal of Pharmacology, 2007, 342-352, 150.
Woodward, David et al, Molecular Characterization and Ocular Hypotensive Properties of the Prostanoid EP2 Receptor, Journal of Ocular Pharmacology, 1995, 447-454, 11(3).
Woodward, David et al, Prostaglandin F2α (PGF2α) 1-Ethanolamide: A Unique Local Hormone Biosynthesized From Anandamide, 11th Intl Conf. Advances Prostaglandin & Leukotriene Res.: Basic Sci. & New Clinical Applications—Abstract Book 27, 2000, 1 page.
Woodward, David et al, Replacement of Carboxylic Acid Group of Prostaglandin F2α with a Hydroxyl or Methoxy Substituent Provides Biologically Unique Compounds, British Journal of Pharmacology, Aug. 2000, 1933-1943, 130(8).
Woodward, David et al, Studies on the Ocular Effects of Pharmalogically Novel Agent Prostaglandin F2α 1-OCH3 (AGN 191129), Eicosanoids, 1998, R719.
Woodward, David et al, The Pharmacology of Bimatoprost (LumiganTM), Surv Ophthalmol, 2001, S337-S345, Suppl 4.
Woodward, David, Pharmacological Characterization of a Novel Antiglaucoma Agent, Bimatoprost (AGN 192024), J. Pharmacol. Exp. Ther., Jan. 24, 2003, 772-785, 305 (2).
Xalatan (Latanoprost Ophthalmic Solution) 0.005% Product Insert, 2001, 4 Pages.
Xalatan® Eye Drops, Retrieval Date : Oct. 2, 2010, 3 pages, http://home.intekom.com/pharm/pharmaca/xalatan.html.
Yamaji, K. et al, Prostaglandins E1 and E2, but not F2α or Latanoprost, Inhibit Monkey Ciliary Muscle Contraction, Curr. Eye Res., Aug. 2005, 661-665, 30(8).
Yoelin, Steve et al, Safety, Effectiveness, and Subjective Experience with Topical Bimatoprost 0.03% for Eyelash Growth, Dermatol. Surg., 2010, 638-649, 36.
Zeigler, Tania, Old Drug New Use: New Research Shows Common Cholesterol-Lowering Drug Reduces Multiple Sclerosis Symptoms In Mice, National Institute of Neurological Disorders and Stroke, Jan. 6, 2003, 2 Pages.

(56) References Cited

OTHER PUBLICATIONS

Zimbric, M.L. et al, Effects of Latanoprost of Hair Growth in the Bald Scalp of Stumptailed Macaques, Glaucoma Pharmacology, Cellular Mechanism II, 1999, 3569-B427—Abstract, vol. 40, No. 4.
United States Court of Appeals for the Federal Circuit, *Allergan, Inc., and Duke University v. Apotex Inc., Apotex Corp., Sandoz, Inc., and Hi-Tech Pharmacal Co., Inc.*, 2014, 41 Pages.
Allen by, AC. et al, Mechanism of Action of Acclerants on Skin Penetration, Br. J. Derm, 1969,47-55, 81{Supp. 4).
Bird, Katie, Nano Carriers Enhance Skin Penetration and Antioxidant Effect of CoQ10, Cosmetics design-asia.com, Apr. 8, 2010,1 Page, nla, William Reed Business Media SAS.
Colombe, Laurent et al, Prostaglandin metabolism in human hair follicle, Experimental Dermatology, May 16, 2007, 762-769, 16, US.
Emu Oil Hairloss and Frontal Regrowth, 2010, 4 Pages, www.hairloss-research.org/blog/?p=73.
Ezure, T et al, Involvement of Sonic Hedgehog in Cyclosporine A Induced Initiation of Hair Growth, Journal of Dermatological Science, 2007, 168-170,47.
Fang, Jia-You et al, In Vitro and in Vivo Evaluations of the Efficacy and Safety of Skin Permeation Enhancers Using Flurbiprofen as a Model Drug, International Journal of Pharmaceutics, 2003, 153-166,255.
Green Tea Consumption Grows Hair, Protects Against UV Radiation in Animal Models, 2010, 4 Pages, www.hairloss-research.org/blog/?p=4.
Grice, Jeffrey et al, Relative Uptake of Minoxidil into Appendages and Stratum Corneum and Permeation Through Human Skin in Vitro, Journal of Pharmaceutical Sciences, Feb. 2010, 712-718, 99(2).
Kreilgmrd, Mads, Influence of Microemulsions on Cutaneous Drug Delivery, Advanced Drug Delivery Reviews, 2002, S77-S98, 54 Suppl. 1.
Muller-Rover, Sven et al, A Comprehensive Guide For the Accurate Classification of Murine Hair Follicles in Distinct Hair Cycle Stages, J. Invest Dermatol, 2001, 3-15, 117.
Mura, Simona et al, Penetration Enhancer-Containing Vesicles (PEVs) as Carriers for Cutaneous Delivery of Minoxidil, International Journal of Pharmaceutics, 2009, 72-79, 380.
Saeki, Hideshisa et al, Guidelines for Management of Atopic Dermatitis, Journal of Dermatology, 2009, 563-577, 36.
Scheider, Marlon et al, The Hair Follicle as a Dynamic Miniorgan, Current Biology, 2009, R132-R142, 19.
Titus, Reuben, Aloe Vera—The Magical Plant Amongst Us, 2009, 12 Pages, http://www.scribd.com/doc/19139862/Aloe-VeraMiracle-Plant.
Tobin, Desmond, Aging of the Hair Follicle Pigmentation System, Int. J. Trichology, Jul.-Dec. 2009,83-93,1(2).
Topical Emu Oil and Coconut Oil for Hair Loss—A Potent Combination, 2010, 3 Pages, www.hairloss-research.org/blogl?p=15.
Uno, Hideo et al, Effect of Latanoprost on Hair Growth in the Bald Scalp of the Stump-Tailed Macacque: A Pilot Study, Acta Derm Venereol, 2002, 7-12, 82.
Verma, Do et al, Treatment of Alopecia Areata in the DEBR Model Using Cyclosporin A Lipid Vesicles, Eur. J. Dermatol, 2004, 332-338, 14.
Maurer, M et al,Hair Growth Modulation by Topical Immunophilin Ligands, Amer. J. Path. 1997, 150: 1433-1441 (4).

Fig. 1: Example of the Effect of Bim 0.03% on Eyelash Growth Compared to Vehicle – Post-chemotherapy population Fig. 2 Percentage of Subjects With at Least a 1-Grade Improvement in GEA Score – Post-chemotherapy Fig. 3. Treatment Responders (%) Based on Primary Composite Variable by Month: Post-chemotherapy (Intent-to-treat Population)

Fig. 4. Mean Change From Baseline in Eyelash Length (mm) by Month: Post-chemotherapy Fig 11. Study design, treatments, and subject disposition.
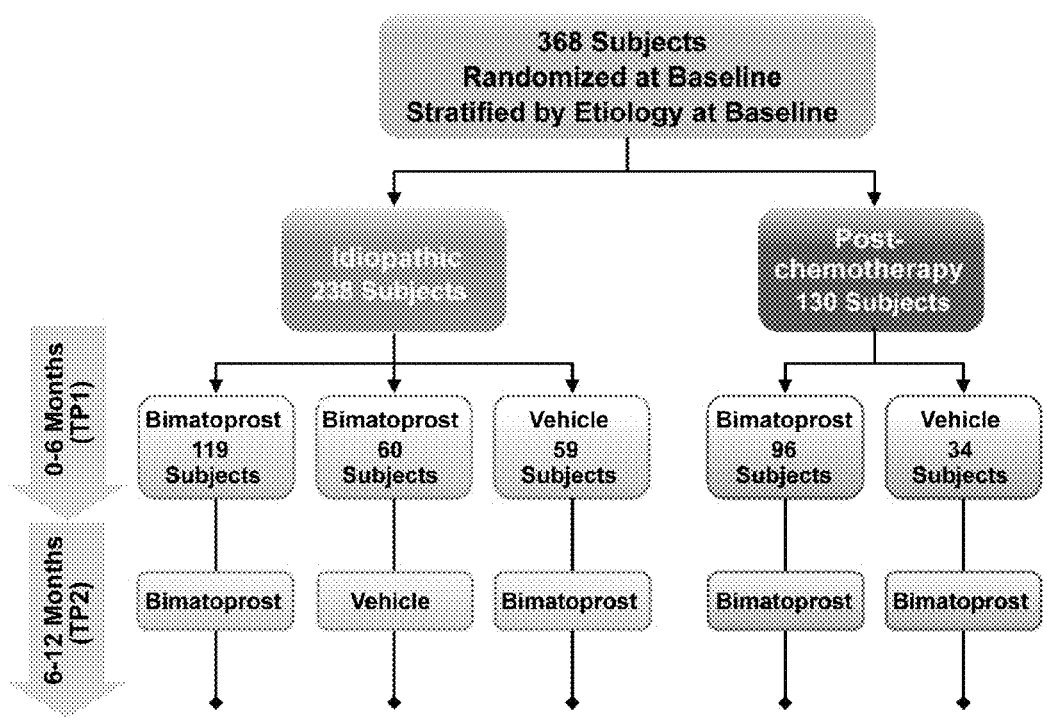

Fig 12. Representative photographs of subjects with hypotrichosis undergoing 6 months of treatment with bimatoprost 0.03% or vehicle. Panel a: Subject with idiopathic hypotrichosis; Panel b: Subject with chemotherapy-induced hypotrichosis.

(a)

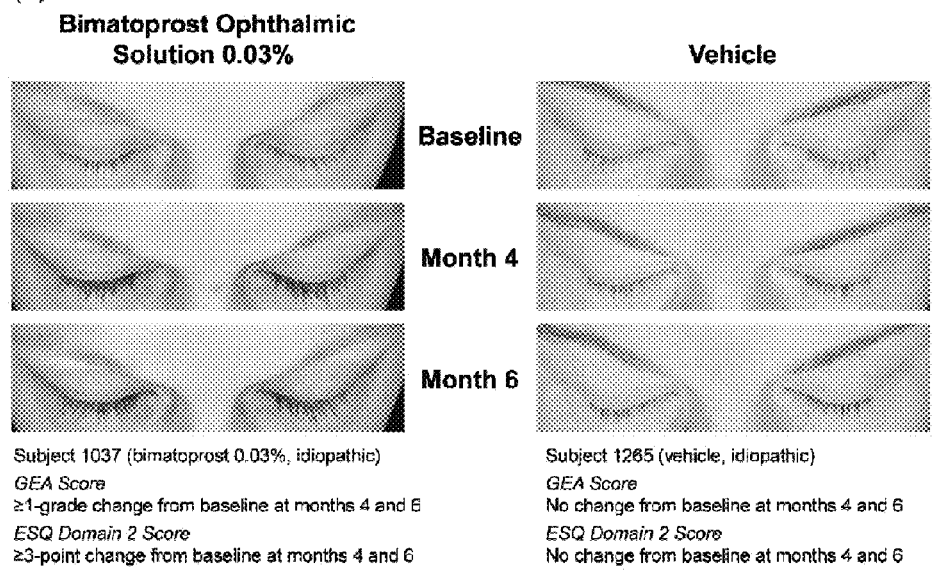

Subject 1037 (bimatoprost 0.03%, idiopathic)
GEA Score
≥1-grade change from baseline at months 4 and 6
ESQ Domain 2 Score
≥3-point change from baseline at months 4 and 6

Subject 1265 (vehicle, idiopathic)
GEA Score
No change from baseline at months 4 and 6
ESQ Domain 2 Score
No change from baseline at months 4 and 6

(b)

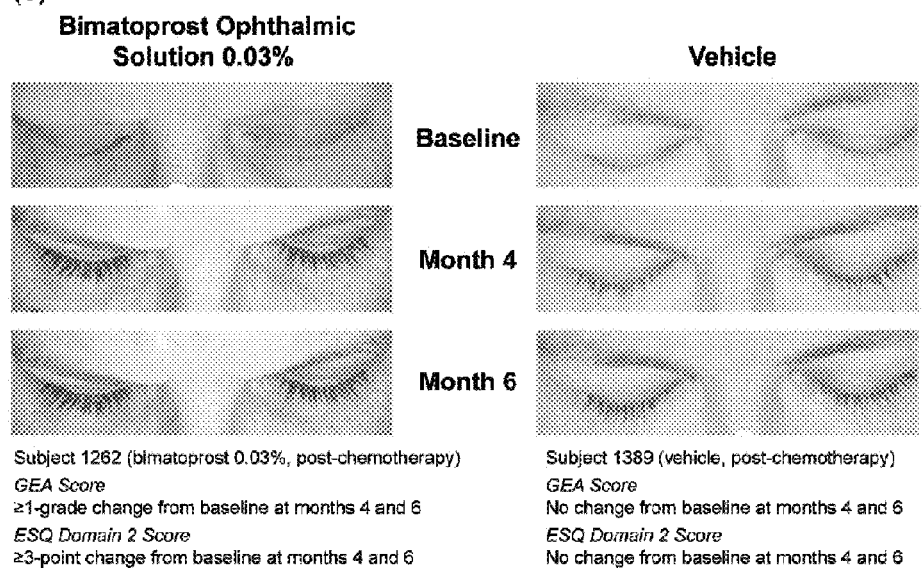

Subject 1262 (bimatoprost 0.03%, post-chemotherapy)
GEA Score
≥1-grade change from baseline at months 4 and 6
ESQ Domain 2 Score
≥3-point change from baseline at months 4 and 6

Subject 1389 (vehicle, post-chemotherapy)
GEA Score
No change from baseline at months 4 and 6
ESQ Domain 2 Score
No change from baseline at months 4 and 6

TOPICAL TREATMENT FOR CHEMOTHERAPY INDUCED EYELASH LOSS OR HYPOTRICHOSIS USING PROSTAMIDE F2 ALPHA AGONISTS

CROSS REFERENCE TO RELATED APPLICATIONS

This application is a continuation-in-part of U.S. patent application Ser. No. 14/199,402, filed Mar. 6, 2014, which is a continuation of U.S. patent application Ser. No. 13/738,732, filed Jan. 10, 2013, which claims priority to U.S. Provisional Application No. 61/611,920, filed Mar. 16, 2012, and U.S. Provisional Application No. 61/584,877, filed Jan. 10, 2012. This application is also a continuation-in-part of U.S. patent application Ser. No. 13/937,512, filed Jul. 9, 2013, which is a continuation of U.S. patent application Ser. No. 13/441,783, filed Apr. 6, 2012, now U.S. Pat. No. 8,632,760, issued Jan. 21, 2014, which is a continuation of U.S. patent application Ser. No. 13/356,284, filed Jan. 23, 2012, now U.S. Pat. No. 8,263,054, issued Sep. 11, 2012, which is a continuation of U.S. patent application Ser. No. 12/425,933, filed Apr. 17, 2009, now U.S. Pat. No. 8,298,518, issued Oct. 30, 2012, which is a continuation of U.S. patent application Ser. No. 11/943,714, filed Nov. 21, 2007, now U.S. Pat. No. 8,038,988, issued Oct. 18, 2011, which is a continuation of U.S. patent application Ser. No. 11/805,122, filed May 22, 2007, now U.S. Pat. No. 8,101,161, issued Jan. 24, 2012, which is a continuation of U.S. patent application Ser. No. 10/345,788, filed on Jan. 15, 2003, now U.S. Pat. No. 7,351,404, issued Apr. 1, 2008, which claims the benefit of U.S. Provisional Application No. 60/354,425, filed on Feb. 4, 2002, all of which are hereby incorporated by reference in their entireties.

FIELD OF THE INVENTION

The present invention is directed to methods and treatments of post-chemotherapeutic hypotrichosis. More specifically, the present invention is directed to the use of compositions comprising bimatoprost for the treatment of post-chemotherapeutic hypotrichosis.

BACKGROUND OF THE INVENTION

Eyelashes, in addition to their contribution to appearance, serve a functional role by protecting sensitive eye structures against foreign particles entering the eye. The nerve plexus that surrounds hair follicles has a very low threshold for excitation (Moses, 1970); as a result, dust or other particles that may come into contact with the eyelash hair fiber are sufficient stimuli to produce a blink reflex, thereby protecting the eye. In terms of the aesthetic function of eyelashes, eyelash prominence has been observed to be related to the attractiveness of individuals, with long, thick eyelashes considered to be a desirable physical attribute with a positive psychological effect (Shaikh and Bodla, 2006).

Inadequate or not having enough eyelashes is known as hypotrichosis of the eyelashes. Etiologies of hypotrichosis of the eyelashes in an adult population include idiopathic hypotrichosis, alopecia-inducing medication (e.g., chemotherapeutic agents) and underlying cutaneous or systemic diseases/conditions (eg, alopecia greata or hypothyroidism).

In healthy adults, eyelash hypotrichosis is often idiopathic and may be related to age. There is an inverse relationship between age and length of eyelashes; younger populations naturally tend to have longer eyelashes, while older populations tend to have shorter eyelashes (Pucci, 2005). For this reason, many otherwise healthy adults experience hypotrichosis as a consequence of aging.

A treatment is available for the natural hypotrichosis condition which may be result of person's genetic makeup or could be age related. Bimatoprost solution 0.03% (LATISSE®) is marketed for the treatment of hypotrichosis of the eyelashes. Bimatoprost is a synthetic prostamide. Topical application of bimatoprost solution can be used in normal healthy adults with inadequate amount of eyelashes or subject who want to further enhance the prominence of their eyelashes (Yoelin, 2010). Treatment with bimatoprost has been demonstrated to increase the percentage of eyelash follicles in anagen, which accounts for its ability to lengthen eyelashes. Bimatoprost-induced stimulation of melanogenesis in melanocytes present in dermal papilla which are responsible for hair shaft pigmentation results in darker eyelashes and, at the same time, appears to increase the size of the dermal papilla and hair bulb, affecting lash thickness and fullness (Cohen, 2010; Fagien, 2010; Law, 2010).

In contrast to the natural eyelash hypotrichosis condition where the hair follicle is normal except it produces shorter and inadequate amount of eyelashes, chemotherapy treatment results in damage to the hair follicle components that make the hair fiber such that after the chemotherapy drug treatment, the natural eyelashes either fall off completely or result in patchy hair loss. Chemotherapeutic agents are well known for their ability to cause hair loss. Other drugs that can cause hair loss to varied degrees include anticoagulants, antithyroid drugs, oral contraceptives, lithium, interferons, antihyperlipidemic drugs, and retinoids (Tosti et al, 1994). Chemotherapy-induced hair loss is known to result from the direct toxic insult to rapidly dividing cells of the hair follicle (Trueb, 2009). During the anagen phase of the hair cycle, the epithelial compartment of the follicle undergoes proliferation, with the greatest proliferative activity occurring in the bulb matrix cells as they build up the hair shaft. When cell mitosis abruptly ceases as a result of cytotoxic therapy, the partially keratinized hair shaft weakens and falls out, resulting in anagen dystrophic effluvium (Ulrich et al, 2008). In addition, some chemotherapeutic agents can cause apoptosis (ie, programmed cell death) in the follicular epithelium resulting in premature transitioning from anagen to catagen phases of the hair cycle; this process is known as telogen effluvium (Ulrich et al, 2008). The consequence of these processes is hair shedding, which can begin within 1 to 3 weeks and is often complete within 1 to 2 months after beginning chemotherapy (Trueb, 2009). Hair loss occurs with an estimated incidence of 65% in adult patients receiving chemotherapy (Trueb, 2009). While eyelash loss can be part of the experience of chemotherapy-induced hair loss (Trueb, 2009), there are no reliable data in the published literature that specifically address the incidence of eyelash loss due to chemotherapy. However, the known mechanism by which chemotherapy induces alopecia indicates that any active hair follicle in anagen would be susceptible, including scalp, body, eyebrow, and eyelash hair.

For most cancer treatments, after the chemotherapy regimen is completed, the patient recovers from the treatment side effects relatively quickly, ie, most side effects of chemotherapy resolve within a few weeks of the last treatment; however, hair growth can continue to be depressed for a period of time. It can take several months to a year, or even longer in some subjects, for hair growth to restore to pre-chemotherapy levels. Moreover, when the hair does recover early, it is generally much finer and thinner than the original hair and can take several hair cycles to restore to the pre-chemotherapy levels.

Hair loss is known to be one of the most psychologically upsetting side effects of cancer therapy (Botchkarev, 2003, Lemieux et al, 2008; Hunt, 2005); it has been described by patients as a constant reminder of their illness and is associated with a loss of control, an altered sense of self, and reduced social functioning (Beisecker et al, 1997; Cowley, 2000; Freedman, 1994; Luoma and Hakamies-Blomqvist, 2004; Richer and Ezer, 2002; Williams et al, 1999). The loss not just of scalp hair but body hair can lead to psychosocial problems such as diminished quality of life expressed as anxiety, depression, and low self-esteem (Ulrich et al, 2008).

In the focus group studies, patients stated that the loss of eyelashes and eyebrows was worse than the loss of scalp hair because the latter could be easily concealed by a wig, whereas there was no way to make their eyelashes look "normal". False eyelashes were not a reasonable treatment in the opinion of the respondents because they did not have enough natural eyelashes to help the glue adhere to their eyelid margins. Moreover, such measures can result in severe irritation and skin damage and are therefore not ideal, especially in the post-chemotherapy population. In focus-group studies, many postchemotherapy patients commented that their eyelashes never fully recovered to their pre-chemotherapy levels. Even though they noticed some re-growth, most complained that their eyelashes were sparse (ie, gaps between lashes), short, and lighter in color.

Currently there are no treatments available for chemotherapy induced eyelash loss. We discovered that treatment with LATISSE (bimatoprost 0.03% solution) restores eyelash growth and prominence quickly compared with the natural course of slower recovery. Thus the protective function of eyelashes is resumed earlier in treated patients as compared to non-treated patients. The postchemotherapy patients treated with bimatoprost 0.03% solution express a higher overall satisfaction with their eyelashes as compared to patients treated with vehicle. Bimatoprost treatment in postchemotherapy patients also restored length, thickness/fullness and darkness of eyelashes.

BRIEF SUMMARY OF THE INVENTION

The present invention is directed to the use of bimatoprost for the use in growing eyelashes in post-chemotherapeutic patients. The present invention is also directed to the use of bimatoprost during chemotherapy to prevent the loss of eyelashes during chemotherapeutic treatment. The present invention is also directed to the use of bimatoprost to prevent the loss of eyelashes prior to the start of chemotherapy. The present invention is also directed to the use of bimatoprost before, during and after chemotherapeutic treatment.

The present invention may be applied as 0.03% w/v bimatoprost available in the commercial product called LATISSE® and may be applied in concentrations 0.3% w/v to 0.001% w/v and including concentrations such as 1.0% w/v, 0.9% w/v, 0.8% w/v, 0.7% w/v, 0.6% w/v, 0.5% w/v, 0.4% w/v, 0.3% w/v, 0.2% w/v, 0.1% w/v, 0.09% 0.08% w/v, 0.07% w/v, 0.06% w/v, 0.05% w/v, 0.04% w/v, 0.03% w/v, 0.02% w/v, 0.01% w/v, 0.009% w/v, 0.008% w/v, 0.007% w/v, 0.006% w/v, 0.005% w/v, 0.004% w/v, 0.003% w/v, 0.002% w/v, 0.001% w/v, 0.009% w/v, 0.008% w/v, 0.007% w/v, 0.006% w/v, 0.005% w/v, 0.004% w/v, 0.003% w/v, 0.002% w/v, and 0.001% w/v bimatoprost.

Bimatoprost may be applied as a solution, emulsion, gel, foam, spray, ointment, cream, or other form suitable for administration to the eyelid margin. Bimatoprost may be in the form of a salt, pro-drug, analogs including esters of bimatoprost. The bimatoprost composition, including LATISSE®, may also be applied in conjunction with other therapeutics known to grow hair such as Minoxidil® and Propecia®.

"Treatment", "treat" or "treating" can refer to curing any disease or condition or reducing or alleviating the symptoms of the disease or condition.

"Prevent", "preventing" or "prevention" can refer to stopping any disease, condition or symptoms or reducing symptoms in a clinically significant manner, particularly as compared to patients receiving no treatment at all.

Some embodiments of the present invention include the following paragraphs:

1) A method of growing eyelashes in chemotherapy patients, the method comprising applying 0.03% w/v bimatoprost at least once a day to the eyelids of a chemotherapy patient from at least one selected from the group consisting of before, during, and after chemotherapeutic treatment wherein patients receiving 0.03% w/v bimatoprost resulted in greater eyelash growth as compared to patients not receiving 0.03% w/v bimatoprost.

2) The method of paragraph 1, wherein 0.03% w/v bimatoprost is applied before starting chemotherapeutic treatment and results in greater eyelash growth in patients as compared to patients not receiving 0.03% w/v bimatoprost.

3) The method of paragraph 2, wherein the method results in eyelashes which are longer or thicker as compared to patients not receiving 0.03% w/v bimatoprost.

4) The method of paragraph 1, wherein the patients receiving 0.03% w/v bimatoprost before starting chemotherapeutic treatment resulted in greater eyelash growth as compared to patients receiving 0.03% w/v bimatoprost during or after chemotherapeutic treatment.

5) The method of paragraph 1, wherein 0.03% w/v bimatoprost is applied to the upper eyelid.

6) The method of paragraph 1, wherein 0.03% w/v bimatoprost is applied to the lower eyelid.

7) The method of paragraph 1, wherein the bimatoprost is added before, during and after chemotherapeutic treatment.

8) A method of preventing or treating eyelashes loss in chemotherapy patients, the method comprising applying 0.03% w/v bimatoprost at least once a day to the eyelids of a chemotherapy patient from at least one selected from the group consisting of before, during, and after chemotherapeutic treatment wherein patients receiving 0.03% w/v bimatoprost resulted in greater eyelash growth as compared to patients not receiving 0.03% w/v bimatoprost.

9) The method of paragraph 8, wherein 0.03% w/v bimatoprost is applied before starting chemotherapeutic treatment and results in greater eyelash growth in patients as compared to patients not receiving 0.03% w/v bimatoprost.

10) The method of paragraph 9, wherein the method results in eyelashes which are longer or thicker as compared to patients not receiving 0.03% w/v bimatoprost.

11) The method of paragraph 8, wherein the patients receiving 0.03% w/v bimatoprost before starting chemotherapeutic treatment resulted in greater eyelash growth as compared to patients receiving 0.03% w/v bimatoprost during or after chemotherapeutic treatment.

12) The method of paragraph 8, wherein 0.03% w/v bimatoprost is applied to the upper eyelid.

13) The method of paragraph 8, wherein 0.03% w/v bimatoprost is applied to the lower eyelid.

14) The method of paragraph 8, wherein the bimatoprost is added before, during and after chemotherapeutic treatment.

15) The method of paragraph 14, wherein the method is applied for at least 12 months after completing chemotherapeutic treatment.

16) The method of paragraph 12 wherein the method is applied prior to receiving chemotherapeutic treatment.

17) The method of paragraph 16, wherein the method is applied for three months prior to receiving chemotherapeutic treatment.

18) The method of paragraph 8 wherein the bimatoprost is in the form of a solution or an emulsion.

19) The method of paragraph 8 wherein the bimatoprost is applied to the upper eyelid, the lower eyelid or both the upper and lower eyelid.

20) The method of paragraph 8 wherein the method is applied after the patient completes chemotherapeutic treatment.

BRIEF DESCRIPTION OF THE DRAWINGS

FIG. 11 shows study design, treatments, and subject disposition;

FIG. 12 shows representative photographs of subjects with hypotrichosis undergoing 6 months of treatment with bimatoprost 0.03% or vehicle; and, FIG. 13 shows Responder rates for idiopathic hypotrichosis and chemotherapy-induced hypotrichosis subpopulations according to study treatments and time points.

DETAILED DESCRIPTION OF THE INVENTION

Example 1

TABLE I

Figure 1:
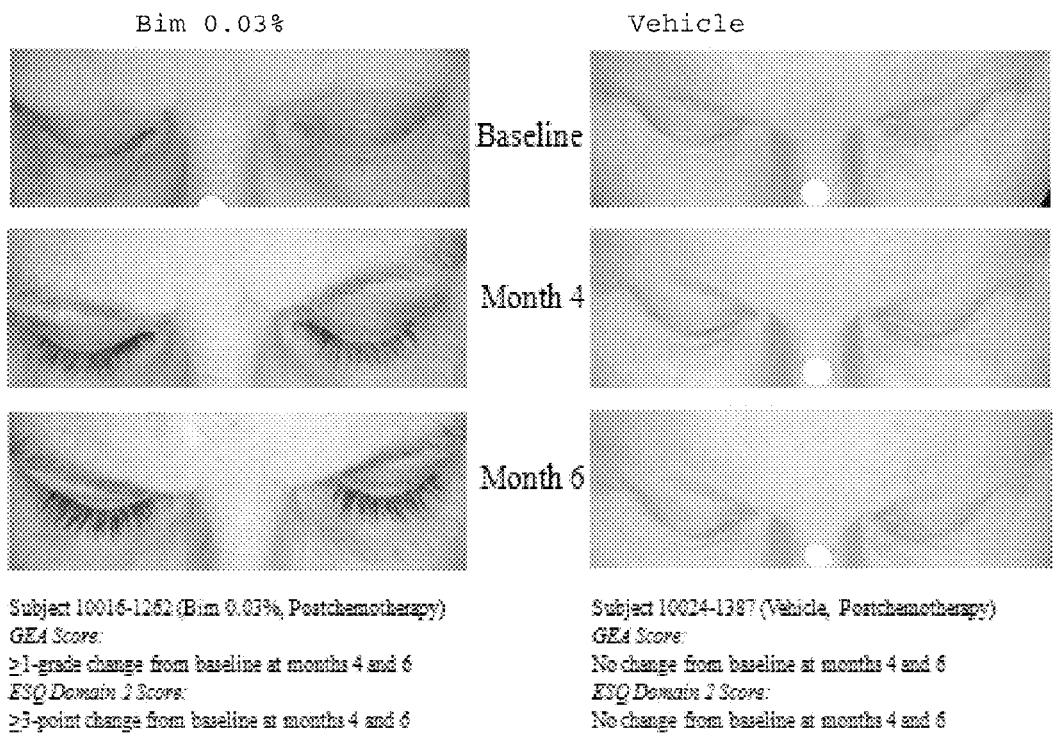
FIG. 1 shows an Example of the Effect of Bim 0.03% on Eyelash Growth Compared to Vehicle—postchemotherapy population.

| List of Components and Quantitative Composition | | | |
|---|---|---|---|
| Ingredients | Concentration (% w/v) | Concentration (mg/mL) | Function |
| Active ingredient | | | |
| Bimatoprost[a] | 0.03 | 0.3 | Active ingredient |
| Other ingredients | | | |
| Benzalkonium chloride[b] | 0.005 | 0.05 | Preservative |
| Sodium phosphate dibasicheptahydrate | 0.268 | 2.68 | Buffering agent |
| Citric acid monohydrate | 0.014 | 0.14 | Buffering agent |
| Sodium chloride | 0.83 | 8.3 | Tonicity agent |
| Hydrochloric acid[c] and/or sodium hydroxide[c] | Adjust to pH 7.2-7.4 | | pH adjuster |
| Purified water | q.s. ad 100% | q.s. ad 1 mL | Vehicle |

Clinical Data:

A clinical study was conducted that demonstrated the clinical benefits of bimatoprost 0.03% solution in treating eyelash loss resulting from chemotherapy treatment.

Study Design and Structure:

This was a 1-year, multicenter, double-masked, randomized, parallel-group study to evaluate the safety and efficacy of bimatoprost solution 0.03% in increasing overall eyelash prominence following dermal application to the upper eyelid margins in normal adults and postchemotherapy adults exhibiting hypotrichosis of the eyelashes. Subjects enrolled in the study were adult subjects at least 18 years of age, with idiopathic or chemotherapy-induced hypotrichosis (Global Eyelash Assessment [GEA] score of 1 or 2) and had a score of 1 or 2 on each of the 3 items (16, 18, and 19) on the Eyelash Satisfaction Questionnaire (ESQ) Domain 2, which represented psychological impact of eyelash loss.

The full 12-month study consisted of 2 distinct 6-month treatment periods, treatment period 1 (TP1) and treatment period 2 (TP2). Eligible post-chemotherapy subjects were randomly assigned in a 3:1 ratio to receive bimatoprost or vehicle for TP1. In TP2, the subjects were either maintained on or switched to bimatoprost treatment.

A total of 130 subjects with chemotherapy-induced hypotrichosis were randomized. Of these, 96 subjects were randomized to the Bim 0.03% group and 34 subjects to the vehicle group. The overall mean age of the postchemotherapy subjects was 50.7 years (range 26 to 76 years), and the majority of the population was Caucasian (79.2%). All except 1 of the subjects enrolled were female (99.2%; 129/130). Per inclusion criteria, all enrolled subjects had a baseline GEA score of 1 (71.3%) or 2 (28.7%), with a similar distribution of GEA scores in both treatment groups at baseline. The mean total score±SD of ESQ Domain 2 for was 3.9±1.23. All enrolled subjects had a baseline ESQ score of 1 or 2 for items 16, 18 and 19 that relates to psychological impact of eyelash loss or hypotrichosis condition.

Primary Composite Efficacy Endpoint:

The primary efficacy endpoint was the proportion of treatment responders at month 4 based on a composite endpoint, defined by: a) at least a 1-grade improvement from baseline in the GEA score, and b) at least a 3-point improvement from baseline in the total score for Domain 2 of the ESQ. The GEA is an investigator assessment of eyelash prominence and the ESQ score is patients own perception of their eyelashes.

6-Month Data:

After 4 months of daily treatment, in the post-chemotherapy subpopulation, the treatment responder rates based on the primary efficacy end point were 37.5% (36/96) in the bimatoprost 0.03% group and 18.2% (6/33) in the vehicle group. Data in the table below shows response rate by visit at month 1, 2, 4, and 6. A continuous improvement in efficacy is observed over the six month time period.

TABLE II

Primary Composite Efficacy Variable: Treatment Responders by Visit

Postchemotherapy population

| Visit | Bim 0.03% (N = 96) | Vehicle (N = 34) | P-value[b] |
|---|---|---|---|
| Month 1 | 6/96 (6.3%) | 2/33 (6.1%) | >0.999[c] |
| Month 2 | 22/96 (22.9%) | 5/33 (15.2%) | 0.344 |
| Month 4 | 36/96 (37.5%) | 6/33 (18.2%) | 0.041 |
| Month 6 | 45/96 (46.9%) | 6/33 (18.2%) | 0.004 |

Figure 2:
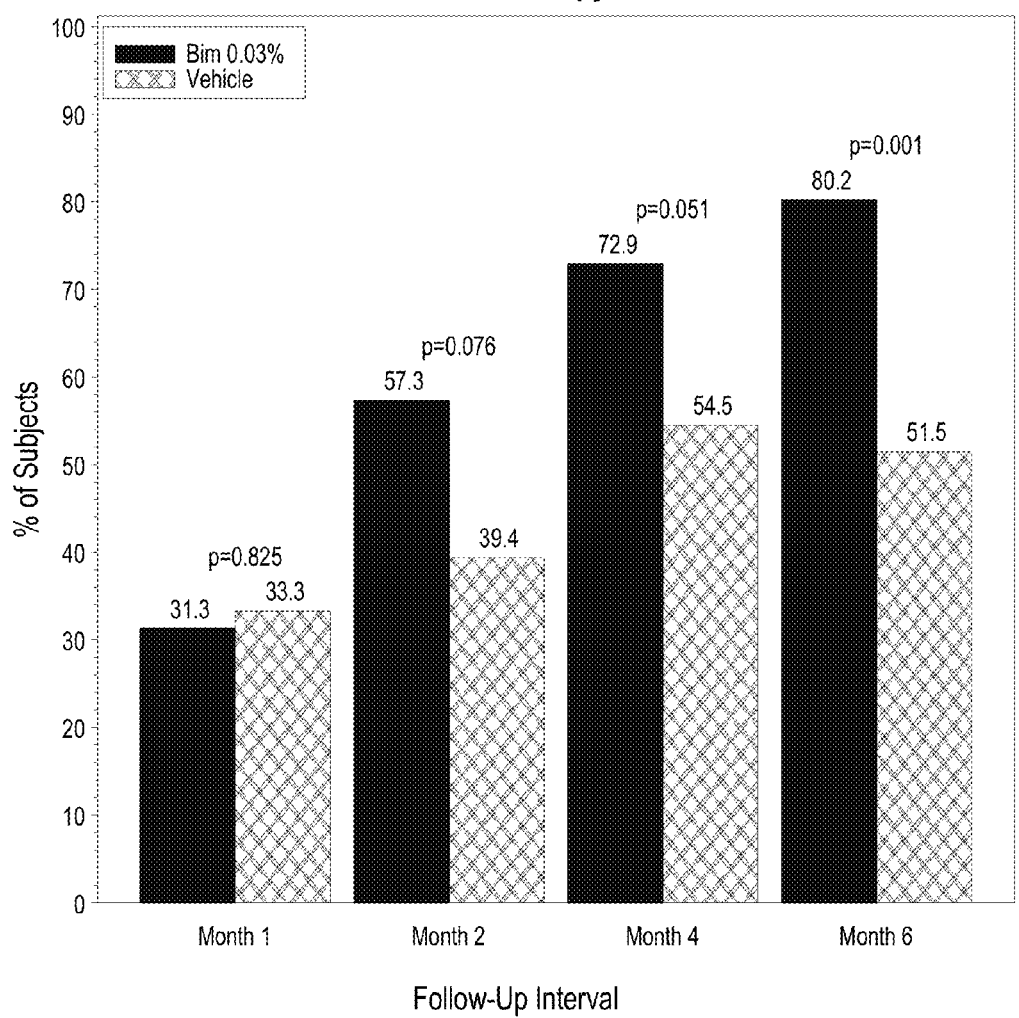
FIG. 2 Percentage of Subjects With at Least a 1-Grade Improvement in GEA Score—Postchemotherapy.

The response rate was also determined solely based on the investigator GEA scoring. As shown in FIG. 1, the Bim 0.03% group had a higher responder rate at the month 2, 4, and 6 visits compared with the vehicle group. The difference in responder rate, based on GEA of eyelash prominence, approached statistical significance at month 4 (p=0.051) and was statistically significant at the month 6 visit (p=0.001). The relatively high responder rate in the vehicle group of the post-chemotherapy population compared to the vehicle group of the normal adult population is attributable to the natural re-growth that occurs to some degree upon completion of chemotherapy treatment. FIG. 2 shows the percentage of subjects with at least a 1-grade improvement in GEA Score—Post-chemotherapy.

Efficacy was also assessed using more conservative criteria of 2-grade improvement in GEA. At month 4, the responder rates for the 2-grade increase in the Bim 0.03% group was 36.5% (35/96) compared to vehicle response of 6.1% (2/33) for this 2 grade increase. In addition to the investigator global assessment (GEA) and subjects own assessment (ESQ), the eyelash length, thickness/fullness and darkness were measures using digital image analysis.

The mean change in eyelash length from baseline at month 4 was 1.48 mm in the Bim 0.03% group and 0.72 mm in the vehicle group. By month 6, the mean change in eyelash length from baseline was 1.99 mm for the Bim 0.03% group and 1.01 mm for the vehicle group.

The mean changes in eyelash thickness from baseline at month 4 were 0.67 $mm^2$ in the Bim 0.03% group and −0.05 $mm^2$ in the vehicle group. By month 6, the mean changes in eyelash thickness from baseline were 0.83 $mm^2$ for the Bim 0.03% group and 0.04 $mm^2$ for the vehicle group.

The mean change from baseline in eyelash darkness was greater in the Bim 0.03% than in the vehicle group. At the month 4 and 6 visits, it was −22.48 and −26.46, respectively, in the Bim 0.03% group and −11.25 and −10.19, respectively, in the vehicle group. The greater negative number on this measure reflects the greater intensity or darkness of eyelashes.

Summary of Efficacy Data on Effect of Bimatoprost on Increasing Eyelash Growth in Post-Chemotherapy Population:

For the primary composite efficacy endpoint, the Bim 0.03% group had a statistically significantly higher responder rate than the vehicle group at month 4 (p=0.041). At month 4, the responder rate was 37.5% (36/96) in the Bim 0.03% group and 18.2% (6/33) in the vehicle group. By month 6, the responder rate in the Bim 0.03% group increased to 46.9% (45/96), whereas there was no change in the vehicle group (18.2%, 6/33).

The Bim 0.03% group had a higher percentage of subjects with at least a 1-grade increase from baseline in GEA score compared to the vehicle group at all follow-up visits. The difference between the 2 groups approached statistical significance at month 4 (p=0.051) and was statistically significantly different at the month 6 visit (p=0.001). At the month 4 visit, 72.9% in the Bim 0.03% group and 54.5% in the vehicle group had at least a 1-grade increase from baseline in GEA score. By month 6, the percentage of responders increased to 80.2% in the Bim 0.03% group, whereas in the vehicle group it decreased to 51.5%.

The percentage of subjects with at least a 1-grade increase from baseline in GEA in the Bim 0.03% group of the postchemotherapy subpopulation (72.9%) was comparable to that of the normal adult subpopulation (74.3%) at month 4. Relative to the vehicle group in the normal adult subpopulation, the vehicle group in the postchemotherapy subpopulation showed higher GEA response at all visits which is likely related to some degree of natural regrowth in the postchemotherapy subpopulation Statistically significant improvements from baseline in upper eyelash length, thickness, and darkness were seen in the Bim 0.03% group compared to the vehicle group at month 4 and month 6.

At month 4, 36.5% of subjects in the Bim 0.03% group of the postchemotherapy subpopulation had at least a 2-grade increase from baseline in GEA scores.

Statistically significant improvements in favor of Bim 0.03% group were observed for ESQ Domains 1 and 3 scores at months 4 and 6. For Domain 2, although the improvements were not statistically significantly different between the two treatment groups, the Bim 0.03% group had a higher mean change in total score from baseline than the vehicle group (2.8 versus 1.7).

Postchemotherapy Population (Safety Summary):

In the postchemotherapy subpopulation, 57.3% (55/96) of subjects in the Bim 0.03% group and 45.5% (15/33) of subjects in the vehicle group reported at least 1 adverse event over the first 6-month study period. Adverse events that were more common in the Bim 0.03% group (more than 5% of subjects) than in the vehicle group were conjunctival hyperaemia, punctate keratitis and eye pruritus. The majority of adverse events were reported as mild or moderate in severity. The treatment-related adverse events were reported by 27.1% (26/96) and 6.1% (2/33) of subjects in the Bim 0.03% and vehicle groups, respectively. Treatment-related adverse events reported by more than 1 subject in the Bim 0.03% group were conjunctival hyperaemia (12 subjects), punctate keratitis (7 subjects), eyelids pruritus (3 subjects), eye pruritus (3 subjects), skin hyperpigmentation (3 subjects) and eyelid irritation (2 subjects). The 2 treatment-related adverse events reported in the vehicle group were punctate keratitis (1 subject) and eyelids pruritus (1 subject).

None of the treatment-related adverse events were reported as severe, and none of them led to study or treatment discontinuation.

12-Month Data:

For subjects receiving bimatoprost for up to 12 months (Bim/Bim group), the efficacy demonstrated for the composite end point, ie, the proportion of responders increased from month 6 to the month 12 period as shown in the figure below. The responder rate, based on the primary efficacy composite measure, increased from 46.9% at month 6 to 61.5% at month 12. These data indicate continuous improvement seen in the postchemotherapy population through month 12 of treatment. These data also demonstrate that efficacy is maintained over 12 months of daily exposure, with no indication for development of any resistance to the treatment.

Figure 3:
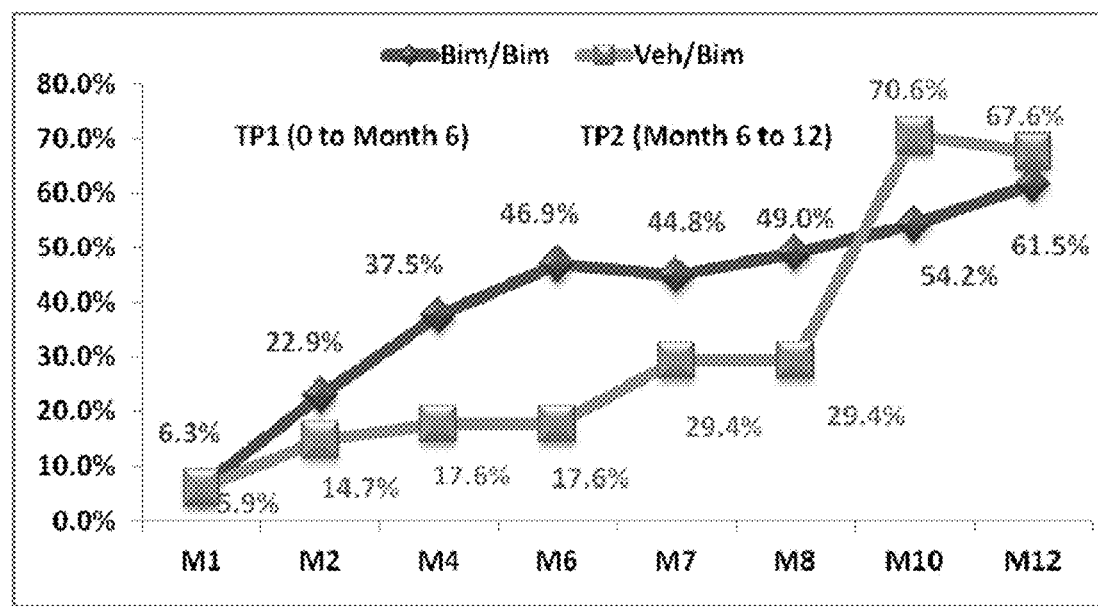
FIG. 3 Shows treatment Responders (%) Based on Primary Composite Variable by Month: Postchemotherapy (Intent-to-treat Population)

Subjects that received vehicle in the first 6 months of treatment and then switched to bimatoprost in TP2 (Veh/Bim groups), the drug effect was rapidly realized, the responder rate increased from 17.6% (6/34) at month 6 to 67.6% (23/34) at month 12 as shown in FIG. 3.

Eyelash Length:

For the idiopathic hypotrichosis subpopulation treated for up to 12 months with bimatoprost, the mean eyelash length at baseline was 5.69 mm and increased by 1.44 mm at month 6 of treatment, and then remained fairly constant throughout the treatment period. This corresponds to a mean percent increase from baseline of 26.17% at month 6 and 25.86% at month 12, and a median percent increase from baseline of 22.4% at month 6 and 22.63% at month 12 This indicates that eyelash length increase is maintained, with no evidence of development of resistance, from month 6 through 12 of daily treatment.

Mean Change±Standard Deviation (SD) from
Baseline in Eyelash Length (Mm)

|  | Postchemotherapy | |
| --- | --- | --- |
| TP1/TP2/Visit[a] | Bim/Bim (N = 96) | Veh/Bim (N = 34) |
| Baseline | 4.86 ± 1.189 | 4.65 ± 1.413 |
| Month 4 | 1.48 ± 1.391 | 0.72 ± 1.396 |
| Month 6 | 1.99 ± 1.557 | 1.01 ± 1.275 |
| Month 10 | 2.14 ± 1.455 | 2.27 ± 1.439 |
| Month 12 | 2.01 ± 1.504 | 2.07 ± 1.442 |

Figure 4:
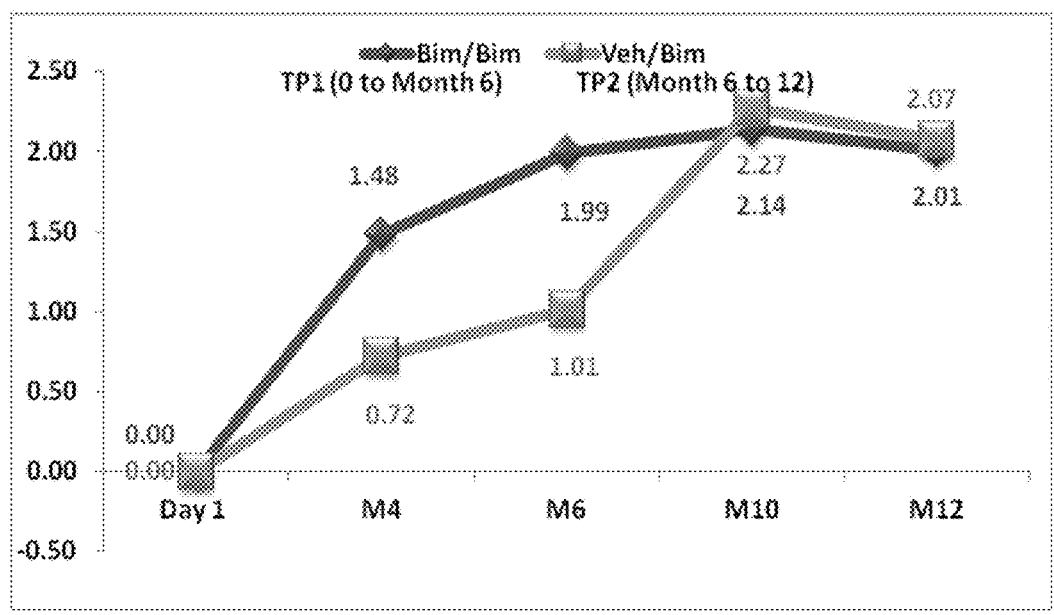
FIG. 4 Shows Mean Change From Baseline in Eyelash Length (mm) by Month: Postchemotherapy.

Bim = bimatoprost 0.03%;
TP1 = treatment period 1 (day 1 to month 6);
TP2 = treatment period 2 (month 6 to 12);
Veh = vehicle For the post-chemotherapy subjects treated for up to 12 months with bimatoprost, the mean eyelash length at baseline was 4.86 mm and increased by 1.99 mm at month 6 of treatment, and then remained fairly constant throughout the treatment period. This corresponds to a mean percent increase from baseline of 48.08% at month 6 and 49.88% at month 12, and a median percent increase from baseline of 37.84% at month 6 and 39.08% at month 12), again indicating that eyelash length increase is maintained, with no evidence of loss of effect upon continuous daily treatment from months 6 through 12 as shown in FIG. 4.

For the postchemotherapy subjects treated for up to 12 months with bimatoprost, the mean thickness at baseline was 0.39 mm$^2$, which increased by 0.83 mm$^2$ at month 6 of treatment, and then remained fairly constant throughout the treatment period. This corresponds to a mean percent increase from baseline of 428% at month 6 and 478% at month 12, and a median percent increase from baseline of 245% at month 6 and 212% at month 12, again the eyelash thickness increase was maintained, with no evidence of loss of effect upon continuous daily treatment from month 6 through 12.

Mean Change±Standard Deviation (SD) from
Baseline in Average Progressive Eyelash Thickness
(mm$^2$)

At Least a 2-Grade Increase in Global Eyelash
Assessment Score

|  | Postchemotherapy | |
| --- | --- | --- |
| TP1/TP2/Visit[a] | Bim/Bim (N = 96) | Veh/Bim (N = 34) |
| Baseline | 0.39 ± 0.302 | 0.67 ± 0.995 |
| Month 4 | 0.67 ± 0.514 | −0.05 ± 0.955 |
| Month 6 | 0.83 ± 0.576 | 0.04 ± 1.009 |
| Month 10 | 0.88 ± 0.516 | 0.63 ± 1.042 |
| Month 12 | 0.85 ± 0.575 | 0.58 ± 1.085 |

Bim = bimatoprost 0.03%;
TP1 = treatment period 1 (day 1 to month 6);
TP2 = treatment period 2 (month 6 to 12);
Veh = vehicle A secondary analysis of the GEA component of the primary efficacy variable using a more stringent criterion was the percentage of subjects who experienced at least a 2-grade increase and a 3-grade increase from baseline on the GEA scale. For postchemotherapy hypotrichosis subjects treated for up to 12 months with bimatoprost, 45.8% of the subjects had at least a 2-grade increase in GEA at month 6, which increased to 57.3% at month 12. This indicates a progressive increase in eyelash prominence from month 6 to 12.

The postchemotherapy subjects treated with vehicle for the first 6 months and then switched to bimatoprost treatment (Veh/Bim) had only 8.8% (3/34) of the subjects with a 2-grade GEA increase at month 6; this increased to 50% by month 10 (4 months after starting bimatoprost treatment) and to 52.9% by month 12.

Efficacy in the post-chemotherapy hypotrichosis population showed a gradual increase in the number of responders through 12 months of treatment. Though an early peak in the percent responders was observed at month-6 (46.9%) and a minimal change between months-6 and -8, there was a gradual further increase to 54.2% at month-10 and an increase to 61.5% at month-12, indicating a continuous improvement in this population. A similar gradual increase in the percent responders was noted based on at least 1-grade increase in GEA or at least 3-point increase in ESQ Domain-2 from month-6 to the month-12 treatment. The GEA responders increased from 80.2 to 90.6% and the ESQ Domain-2 responders increased from 47.9 to 63.5% between month-6 and -12.

Majority of the common adverse events observed for the entire 12-month period were from the first 6 months of treatment, indicating that continuous treatment does not lead to increased incidence of adverse events. For example, the incidence rate for three of the most common AEs in the postchemotherapy population, conjunctival hyperaemia, punctate keratitis and eyelids pruritus was 15.6%, 8.3% and 3.1%, respectively, in the first 6 months of treatment vs. only 1.1% (new AE) for each of these three events for months 6-12.

Example 2

This is a long-term safety and efficacy study of bimatoprost ophthalmic solution 0.03% (LATISSE®) bimtoprost carried out in idiopathic and post-chemotherapy hypotrichosis populations. In this study, eyelash loss from chemotherapy was studied.

Study Design:

A one-year, multicenter, randomized, double-masked, vehicle-controlled study. Adult post-chemotherapy and idiopathic eyelash hypotrichosis subjects were enrolled based on their score of 1 or 2 on a four point ordinal Global Eyelash Assessment (GEA) scale, and in addition having a low score on a PRO measure associated with 'psychological impact' of the condition, a domain-2 of the Eyelash Satisfaction Questionnaire (ESQ). The study involved two treatment periods of six months each. In the first treatment period, subjects for both populations were randomized 3:1 for QD bimatoprost: vehicle treatment. In the second 6-month treatment period, all subjects were moved to bimatoprost treatment, except for a group of bimatoprost treated idiopathic hypotrichosis subjects (n=55) who were switched to vehicle to investigate the effect of drug discontinuation. The study included 9 visits over the 12-month treatment period. The primary end point was the proportion of responders within each treatment group based on a composite measure of GEA and ESQ Domain-2 (investigator assessed eyelash prominence and subject's assessment of 'psychological impact' related to eyelashes) at month-4.

Results:

A total of 368 subjects were randomized, 238 idiopathic and 130 post-chemotherapy. The primary efficacy end point was met for both idiopathic and post-chemotherapy populations. A baseline, majority of the post-chemotherapy subjects showed sparse, patchy eyelashes to near complete loss. In both populations, majority of the subjects (>70%) demonstrated increased eyelash prominence (≥1 grade GEA improvement) at month-4 following daily bimatoprost treatment. There were no drug related serious adverse events in the study.

In subjects with idiopathic hypotrichosis, 40.2% efficacy (a greater than 1-grade increase in GEA score and at least 3 point improvement in ESA domain score) was achieved at month 4, while only 6.8% of the vehicle treated subjects had a similar increase in GEA after 4 months. Efficacy was maintained over the 12-month trial period. After drug discontinuation, efficacy was maintained for about 2 months, and return to near pre-treatment levels occurred 4 to 6 months after discontinuation. In subjects with chemotherapy-induced hypotrichosis, 37.5% increase in efficacy was achieved at month 4 whereas only 18.2% of the vehicle treated subjects had a similar increase in GEA after 4 months. Efficacy was enhanced over the 12-month trial period.

In subjects with idiopathic hypotrichosis, 74.3% of the bimatoprost treated subjects had an increase in GEA of greater than 1 after 4 months, while only 13.6% of the vehicle treated subjects had a similar increase in GEA after 4 months. In subjects with chemotherapy-induced hypotrichosis, 72.9% of those receiving bimatoprost treatment had an increase of GEA of greater than 1 after 4 months, while 54.5% of the vehicle-treated subjects had a similar increase in GEA after 4 months (due to the natural untreated regrowth of eyelashes after cessation of chemotherapy). Both populations had statistically significant improvements in eyelash length, thickness/fullness, and darkness by bimatoprost compared with vehicle at months 4 and 6 (not shown).

The changes in eyelash length, thickness and darkness are shown in the table below:

Eyelash Length, Thickness, and Darkness

Percent Change from Baseline at Month 4

| Endpoint | Idiopathic Hypotrichosis (mean % change) | | | Chemotherapy-Induced Hypotrichosis (median % change) a | | |
|---|---|---|---|---|---|---|
| | Bim 0.03% | Vehicle | P-value | Bim 0.03% | Vehicle | P-value |
| Length | 22.90% | −4.90% | <.001 | 28.50% | 11.30% | 0.022 |
| Thickness | 95.90% | −7.20% | <.001 | 180.10% | 25.00% | 0.002 |
| Darkness[b] | −15.70% | 1.40% | <.001 | −14.40% | −5.70% | 0.012 | a Median values are provided because data from the post-chemotherapy subpopulation did not follow a normal distribution.
[b] Negative change from baseline indicates darker lashes.

Figure 5:
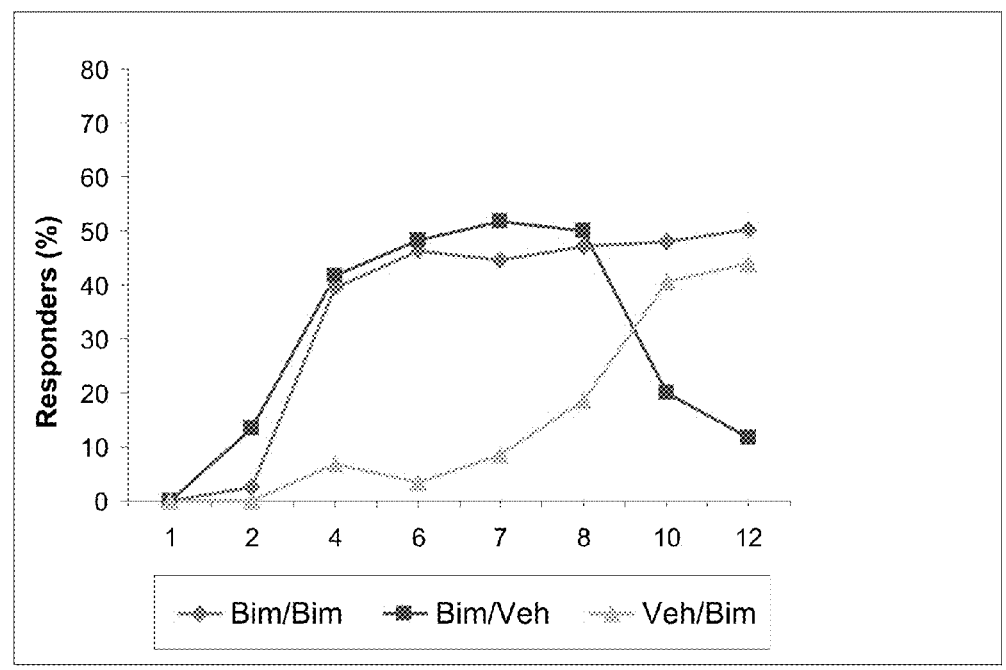
FIG. 5 is a plot of primary composite efficacy for the duration of the trial for subjects with idiopathic hypotrichosis.

Results for Subjects with Idiopathic Hypotrichosis:

FIG. 5 is a plot of primary composite efficacy for the duration of the trial. Bim/Bim indicates subjects receiving bimatoprost for 12 months. Bim/Veh indicates subjects receiving bimatoprost for 6 months followed by vehicle for 6 months. Veh/Bim indicates subjects receiving vehicle for 6 months followed by bimatoprost for 6 months.

Figure 6:
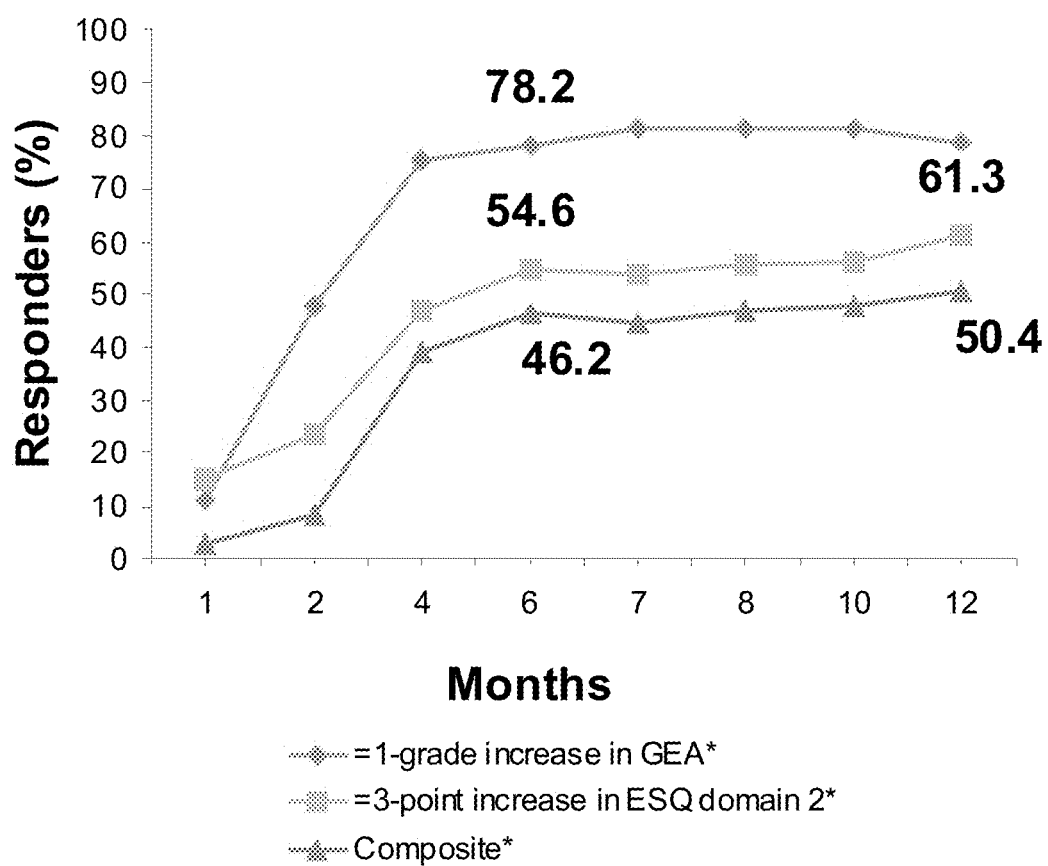
FIG. 6 is a plot of responder rates in bimatoprost-treated subjects by individual components of the primary composite efficacy measure for the duration of the for subjects with idiopathic hypotrichosis.

FIG. 6 is a plot of responder rates in bimatoprost-treated subjects by individual components of the primary composite efficacy measure for the duration of the trial. FIG. 6 shows a GEA response rate of about 75% to about 80% and a maintenance of the effect and/or continuous improvement up to month 12.

Figure 7:
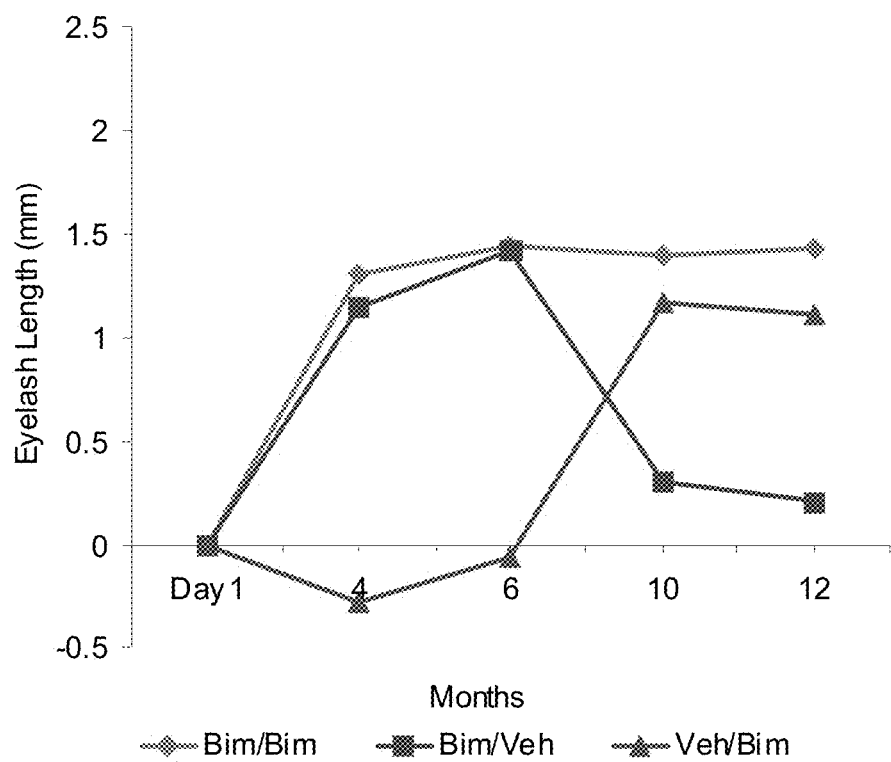
FIG. 7 is a plot of improvement in eyelash length for the duration of the trial for subjects with idiopathic hypotrichosis.

FIG. 7 is a plot of improvement in eyelash length for the duration of the trial. Bim/Bim indicates subjects receiving bimatoprost for 12 months. Bim/Veh indicates subjects receiving bimatoprost for 6 months followed by vehicle for 6 months. Veh/Bim indicates subjects receiving vehicle for 6 months followed by bimatoprost for 6 months.

Figure 8:
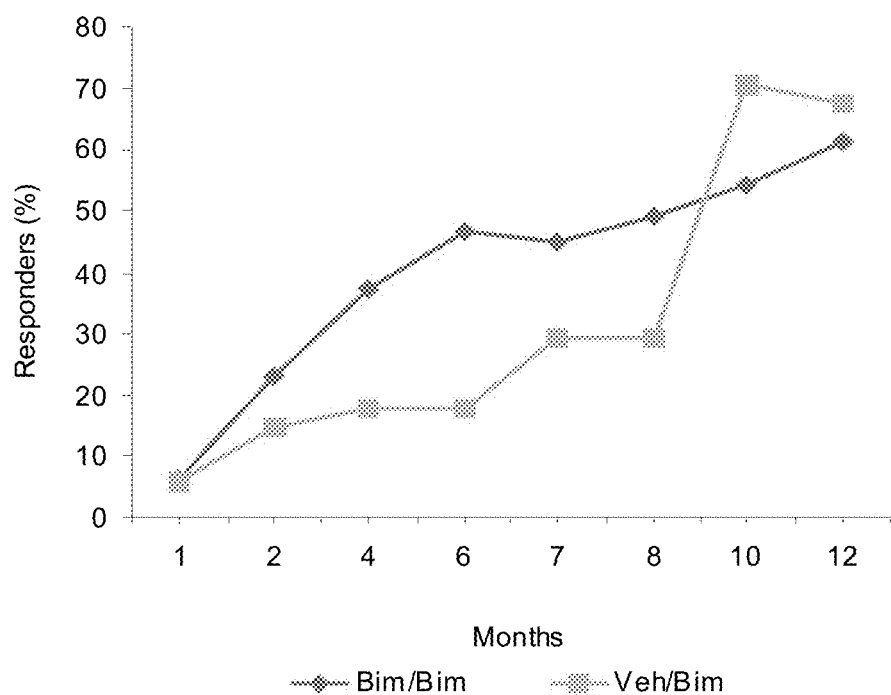
FIG. 8 is a plot of primary composite efficacy for the duration of the trial for subjects with chemotherapy-induced hypotrichosis.

Results for Subjects with Chemotherapy-Induced Hypotrichosis:

FIG. 8 is a plot of primary composite efficacy for the duration of the trial. Bim/Bim indicates subjects receiving bimatoprost for 12 months. Bim/Veh indicates subjects receiving bimatoprost for 6 months followed by vehicle for 6 months.

Figure 9:
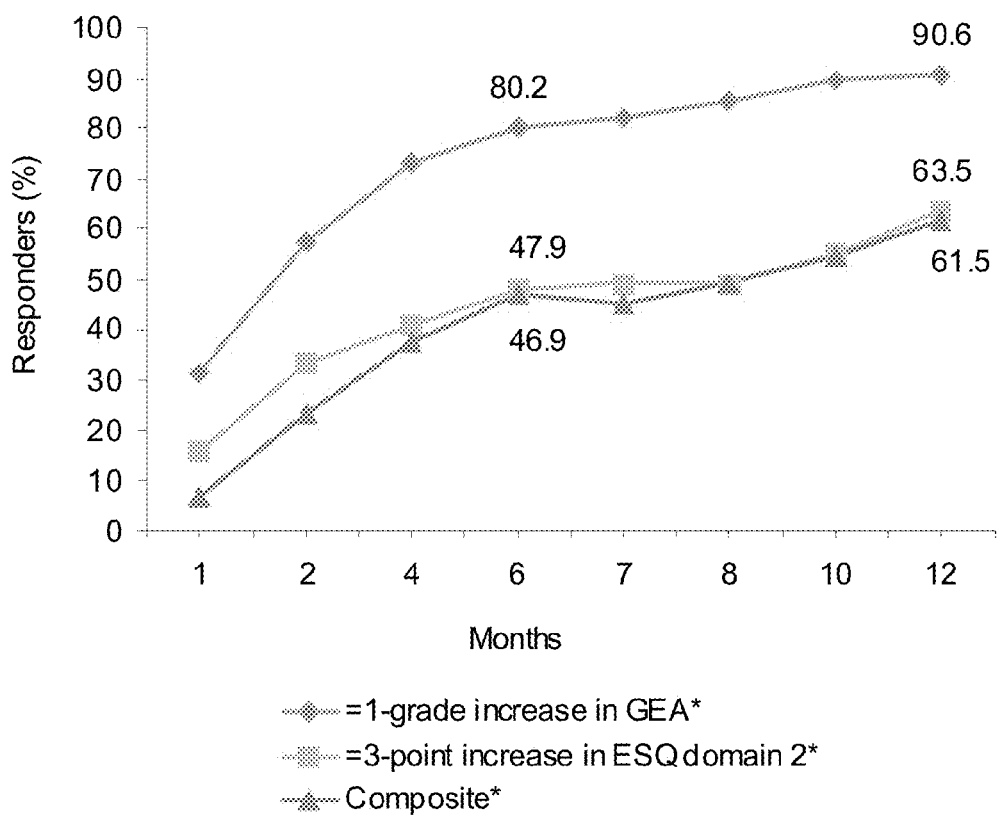
FIG. 9 is a plot of responder rates in bimatoprost-treated subjects by individual components of the primary composite efficacy measure for the duration of the trial for subjects with chemotherapy-induced hypotrichosis.

FIG. 9 is a plot of responder rates in bimatoprost-treated subjects by individual components of the primary composite efficacy measure for the duration of the trial. FIG. 9 shows a GEA response rate of about 80% that is similar to the idiopathic population, and continuous improvement up to month 12.

Figure 10:
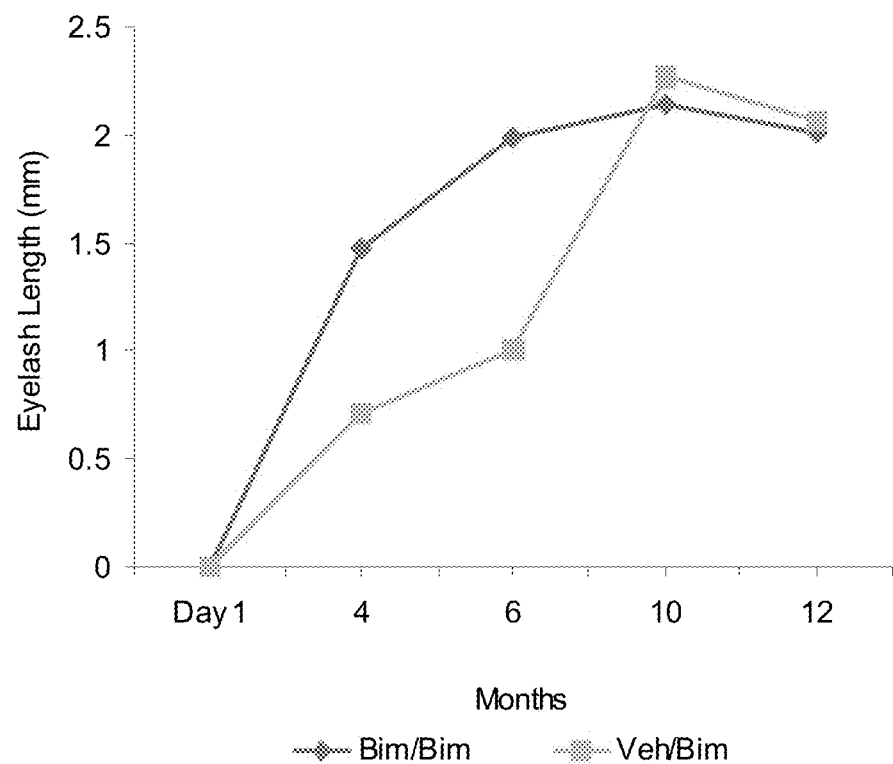
FIG. 10 is a plot of improvement in eyelash length for the duration of the trial for subjects with chemotherapy-induced hypotrichosis.

FIG. 10 is a plot of improvement in eyelash length for the duration of the trial. Bim/Bim indicates subjects receiving bimatoprost for 12 months. Bim/Veh indicates subjects receiving bimatoprost for 6 months followed by vehicle for 6 months.

Over 12 months of bimatoprost treatment, the most common adverse events (>5%) in either idiopathic or post-chemotherapy population were conjunctival hyperaemia, punctate keratitis, eyelid pruritus, erythema of eyelids, and eye pruritus. Common adverse events (conjunctival hyperaemia, punctate keratitis, and eye pruritus) were reported at a higher rate in the post-chemotherapy population. This may have been related to the enduring effect of chemotherapy drugs on eyes. Common ocular and dermal adverse events occurred at a lower rate in the second 6-month trial period (months 6-12) compared with the first 6-month trial period. No drug-related serious adverse occurred in either subpopulation.

| | 0 to 12 Months | | 0 to 6 Months | | 6 to 12 Months | |
|---|---|---|---|---|---|---|
| | Idiopathic Hypotrichosis (N = 118) | Post-Chemotherapy (N = 96) | Idiopathic Hypotrichosis (N = 118) | Post-Chemotherapy (N = 96) | Idiopathic Hypotrichosis (N = 106) | Post-Chemotherapy (N = 89) |
| Eye disorders, n (%) | | | | | | |
| Conjunctival hyperaemia | 10 (8.5) | 16 (16.7) | 7 (5.9) | 15 (15.6) | 4 (3.8) | 1 (1.1) |
| Punctate keratitis | 3 (2.5) | 9 (9.4) | 3 (2.5) | 8 (8.3) | 0 (0.0) | 1 (1.1) |
| Eyelids pruritus | 7 (5.9) | 3 (3.1) | 6 (5.1) | 3 (3.1) | 1 (0.9) | 1 (1.1) |
| Erythema of eyelid | 6 (5.1) | 3 (3.1) | 2 (1.7) | 1 (1.0) | 5 (4.7) | 2 (2.2) |
| Eye pruritus | 1 (0.8) | 6 (6.3) | 1 (0.8) | 5 (5.2) | 0 (0.0) | 1 (1.1) |
| Skin and subcutaneous disorders, n (%) | | | | | | |
| Skin hyperpigmentation | 2 (1.7) | 5 (5.2) | 0 (0.0) | 3 (3.1) | 2 (1.9) | 2 (2.2) |

Conclusions:

Bimatoprost ophthalmic solution 0.03% significantly increased eyelash growth in subjects with idiopathic as well as chemotherapy-induced hypotrichosis as measured by the primary composite endpoint (≥1-grade increase in the GEA score AND at least 3-point improvement in ESQ domain-2 score at week 16) and all secondary endpoints (eyelash length, thickness/fullness, and darkness). Bimatoprost treatment effects were maintained through the 12-month trial period. Bimatoprost treatment was safe and well-tolerated in the 2 populations. No new safety signals were detected in the 6- to 12-month trial period. Fewer common ocular and dermal AEs occurred in the second 6-month period than in the first 6 months of bimatoprost treatment. Efficacy was maintained for about 2 months after bimatoprost discontinuation; return to near pre-treatment levels occurred at about 4 to 6 months after discontinuation. Thus, daily application of bimatoprost ophthalmic solution to the eyelid margin over a one-year period was found to be safe, well tolerated and effective in both idiopathic and post-chemotherapy populations as assessed by several safety and efficacy measures.

Example III

Objective

To evaluate long-term safety and efficacy of bimatoprost among subjects with idiopathic or chemotherapy-induced hypotrichosis.

Methods:

This multicenter, double-masked, randomized, parallel-group study included two 6-month treatment periods. Subjects with idiopathic hypotrichosis were randomized to 3 treatment groups: 1) treatment period 1 (TP1) and TP2: bimatoprost; 2) TP1: bimatoprost; TP2: vehicle; and 3) TP1: vehicle; TP2: bimatoprost. Subjects with chemotherapy-induced hypotrichosis were randomized to 2 treatment groups: 1) TP1: bimatoprost or vehicle; and 2) TP2: bimatoprost. The primary endpoint was a composite of at least a 1-grade improvement in investigator-assessed Global Eyelash Assessment (GEA), and at least a 3-point improvement in subject-reported Eyelash Satisfaction Questionnaire (ESQ) Domain 2 (self-perceived confidence, attractiveness, and professionalism) at month 4. Secondary measures included digitally assessed eyelash characteristics (i.e., eyelash length, fullness, and darkness).

Results:

The study randomized 368 subjects. The primary efficacy endpoint was met in both populations (responder rates: idiopathic: 40.2% bimatoprost vs. 6.8% vehicle; post-chemotherapy: 37.5% bimatoprost vs. 18.2% vehicle). Efficacy by month 6 was maintained (idiopathic) or enhanced (post-chemotherapy) at 12 months. Treatment effects were maintained for approximately 2 months but markedly diminished 4 to 6 months following treatment cessation in subjects with idiopathic hypotrichosis. No drug-related serious adverse events were reported.

Conclusions:

Daily treatment with bimatoprost ophthalmic solution 0.03% for 1 year was effective and well tolerated in subjects with idiopathic and chemotherapy-induced hypotrichosis.

Materials and Methods:

This was a 1-year, multicenter, double-masked, randomized, parallel-group study of 1-year treatment duration with two 6-month treatment periods. Two subpopulations evaluated in the study included subjects with idiopathic hypotrichosis and those with hypotrichosis caused by recent chemotherapy. Additionally, the effect of drug discontinuation was studied in subjects with idiopathic hypotrichosis.

The study consisted of 9 visits and 2 telephone visits over 12 months. Treatment period 1 (TP1) extended from screening to month 6, including 6 visits: screening/baseline (day −14 to 1), telephone visit (week 1), and months 1, 2, 4, and 6. Treatment period 2 (TP2) began at the 6-month visit and included visits at months 7, 8, 10, and 12/early termination) and 1 telephone visit (1 week post-month 6).

Idiopathic hypotrichosis subjects were randomized to 3 treatment arms in a 2:1:1 ratio: bimatoprost during both treatment periods; vehicle in TP1 and bimatoprost in TP2; and bimatoprost in TP1 and vehicle in TP2. Chemotherapy-induced hypotrichosis subjects were randomized in a 3:1 ratio to receive bimatoprost during both treatment periods or vehicle in TP1 followed by bimatoprost in TP2.

Male or female subjects at least 18 years of age who met these criteria were eligible for inclusion in the study: a score of 1 or 2 on the clinician-graded global eyelash assessment ("GEA"); a score of 1 (very much disagree) or 2 (disagree) on each of 3 items (16 [confidence], 19 [attractiveness], and 18 [professionalism]) on the subject-assessed eyelash satisfaction questionnaire ("esq"); best-corrected visual acuity ("bcva") score equivalent to a snellen acuity of 20/100 or better in each eye; and intraocular pressure ("iop") 20 mm hg or less in each eye. Subjects in the chemotherapy-induced hypotrichosis population also met the following inclusion criteria: inadequate eyelashes after completing chemotherapy; treatment for solid tumor type stage 1, 2, or 3a cancer; last chemotherapy treatment at least 4 to less than 16 weeks prior to baseline; and considered free of cancer. Key exclusion criteria included subjects with any eye disease or abnormality or a history of eye surgery.

This study was conducted in accordance with the International Conference on Harmonization Guideline for Good Clinical Practice and the Declaration of Helsinki Local ethical committee approval was obtained prior to study initiation. Informed consent was obtained from all subjects prior to any study-related procedure.

Subjects placed 1 drop of study treatment (i.e., bimatoprost 0.03% or vehicle) onto a sterile single-use-per eye applicator and applied it to the upper eyelid margin of 1 eye; a second applicator was used for the contralateral eye. Treatment was applied once daily in the evening throughout the study. The primary efficacy measure was the proportion of treatment responders based on a composite endpoint at month 4, defined a priori as: at least a 1-grade improvement from baseline in the GEA score (4-point photonumeric scale of eyelash prominence based on these descriptors: minimal, moderate, marked, and very marked), and at least a 3-point improvement from baseline in the total score for Domain 2 of the ESQ. Domain 2 consists of questions that evaluate subjects' feelings of confidence, attractiveness, and professionalism rated on a 5-point Likert-type scale (1, very much disagree; 2, disagree; 3, neutral; 4, agree; 5, very much agree) with higher scores indicating a higher degree of subject-reported satisfaction with the subjective attributes of the eyelashes.

Secondary efficacy measures were based on digital image analysis (DIA) of eyelash characteristics: upper eyelash length (millimeters [mm]), thickness ($mm^2$), and darkness (intensity units). For darkness, a negative value in terms of change from baseline indicated darker eyelashes.

Safety measures included adverse events (AEs), ophthalmic examination (ophthalmoscopy [dilated], biomicroscopy, IOP, iris color assessment, and BCVA). AEs were monitored throughout the study by the investigator.

Statistical Analysis

The 6-month primary analysis was based on data from the first 6 months of the study, i.e., TP1, which followed a parallel-group design, allowing for hypothesis testing and between-group comparisons (bimatoprost 0.03% vs. vehicle). Statistical testing was not performed beyond the 6-month analysis because all subjects treated with vehicle during TP2 had been treated with bimatoprost in TP1; hence, there was no vehicle-only control group for TP2. The intent-to-treat (ITT) population consisted of all randomised subjects. The ITT population was used for all efficacy analyses. The safety population consisted of all subjects who received 1 or more doses of study medication. The study was sized to have adequate power to evaluate the primary efficacy variable at month 4 for the overall study population (idiopathic and chemotherapy-induced hypotrichosis subpopulations combined).

GEA and ESQ data were collected at each scheduled visit. The primary efficacy endpoint was defined as the proportion of treatment responders at month 4. The analysis of responders was performed using frequency distributions (counts and percentages). For the 12-month study analysis, the baseline value was the value collected on day 1 or the most recent evaluation prior to day 1. For the TP2 analysis, the baseline value was the value collected at month 6; if month-6 data were missing, data from the most recent previous evaluation were used. For the ITT population analysis, the last observation carried forward method was used to impute missing values in each of the 2 components of the primary composite efficacy variable. Between-group comparisons for TP1 were performed using the Cochran-Mantel-Haenszel test stratified by hypotrichosis etiology. Individual components of the composite efficacy measure as well as at least a 2-grade improvement from baseline GEA score were also assessed at these time points.

Upper eyelash characteristics of length, thickness, and darkness were determined by a validated DIA method. The reliability and reproducibility of DIA have been verified within the acceptance criteria of 0.05% or less of mean coefficient of variance. The principal variables for the secondary efficacy assessments are: change from baseline in upper eyelash length (mm), average progressive eyelash thickness ($mm^2$), and eyelash darkness (intensity units) at months 4, 6, 10, and 12 or early termination. Descriptive statistics of the raw value at baseline and percent change from baseline at follow-up visits were summarized by treatment group for each principal measure of the 3 secondary variables of eyelash characteristics. Between-group comparisons were performed using a van Elteren test stratified by hypotrichosis etiology.

Safety Analysis

The 12-month data were the primary focus of the safety evaluation. Safety data were summarized with descriptive statistics (n, or frequency distributions [counts or percentages]). Biomicroscopic examinations and assessments of iris color, IOP, and BCVA were performed for each subject at screening/baseline and months 1, 2, 4, 6, 8, and 12 (or early termination prior to month 12); ophthalmoscopic examinations (dilated) were performed at screening/baseline and months 6 and 12 (or early termination prior to month 12). Two IOP measurements were taken for each eye at each visit; a third measurement was taken if the difference between the first 2 measurements was more than 2 mm Hg. The average or median IOP was determined in the event that 2 or 3 measurements were made, respectively. The IOP value analyzed at each visit was the average IOP of the subject's 2 eyes. Change and percent change from baseline in IOP were summarized by descriptive statistics. Between-group comparison will be performed using the 1-way analysis of variance.

Iris color assessments were performed using a 10-category subjective classification: blue, blue-gray, blue/gray-brown, gray, green, green-brown, hazel, brown, dark brown, and other.

Results:

A total of 368 subjects were randomized at 39 sites (32 US centers and 7 European Union centers), of which 238 had idiopathic hypotrichosis and 130 had chemotherapy-induced hypotrichosis. Subject disposition (FIG. 11) and baseline characteristics (Table 1) are provided. Per inclusion criteria, all enrolled subjects had baseline GEA scores of 1 (minimal; 39.8%) or 2 (moderate; 60.2%), with a similar distribution of GEA scores in both treatment groups at baseline, although a greater proportion of subjects in the chemotherapy-induced hypotrichosis subpopulation had baseline GEA scores of 1 compared with subjects in the idiopathic hypotrichosis subpopulation (71.3% vs. 22.7%). The majority of subjects completed the clinical trial with only 14.9% of subjects discontinuing from the study. The most common reason for discontinuation was AEs for idiopathic hypotrichosis and loss to follow-up for chemotherapy-induced hypotrichosis subpopulation.

TABLE III

Overall baseline demographic characteristics (intent-to-treat population)

| Characteristic | Overall (n = 368) | Idiopathic Hypotrichosis (n = 238) | Post-Chemotherapy-Induced Hypotrichosis (n = 130) |
|---|---|---|---|
| Age, y, mean (SD) | 49.8 (10.47) | 49.3 (11.09) | 50.7 (9.22) |
| Sex, n (%) | | | |
| Male | 4 (1.1) | 3 (1.3) | 1 (0.8) |
| Female | 364 (98.9) | 235 (98.7) | 129 (99.2) |
| Race, n (%) | | | |
| White | 305 (82.9) | 202 (84.9) | 103 (79.2) |
| Black | 34 (9.2) | 19 (8.0) | 15 (11.5) |
| Asian | 13 (3.5) | 9 (3.8) | 4 (3.1) |
| Hispanic | 15 (4.1) | 7 (2.9) | 8 (6.2) |
| Other[a] | 1 (0.3) | 1 (0.4) | 0 (0.0) |
| GEA score, n (%) | | | |
| Minimal | 147 (39.3) | 54 (22.7) | 93 (71.5) |
| Moderate | 221 (60.1) | 184 (77.3) | 37 (28.5) |
| Marked | 0 | 0 | 0 |
| Very marked | 0 | 0 | 0 |
| Total ESQ Domain 2, mean (SD) | 4.1 (1.35) | 4.2 (1.40) | 3.9 (1.23) |

ESQ, Eyelash Satisfaction Questionnaire;
GEA, Global Eyelash Assessment;
SD, standard deviation.
[a]Other race: black and white.
Note:
Missing data on total ESQ Domain 2 for 1 post-chemotherapy subject.

Composite and Individual Component Efficacy Measures of Bimatoprost Treatment

During TP1, the primary composite efficacy endpoint at month 4 was met for the overall study population and both subpopulations. The composite efficacy endpoint responder rates at months 4 and 6 were statistically significantly greater for active drug compared with vehicle for both subpopulations (Table 2). The responder rates for subjects with idiopathic hypotrichosis treated with bimatoprost compared with vehicle were 40.2% vs. 6.8% (P<0.001) and 47.5% vs. 3.4% (P<0.001) at months 4 and 6, respectively. Corresponding responder rates for subjects with chemotherapy-induced hypotrichosis were 37.5% vs. 18.2% (P=0.041) at month 4 and 46.9% vs. 18.2% (P=0.004) at month 6. Although a greater vehicle treatment effect was observed in post-chemotherapy subjects who experienced natural eyelash regrowth compared with those with idiopathic hypotrichosis, the results for vehicle-treated groups were consistently lower than the corresponding results from bimatoprost-treated groups across all endpoints. More than 4 of 5 post-chemotherapy subjects were still nonresponders in the placebo group at month 6 after study start.

Statistically significant differences were observed in the responder rates for subjects with idiopathic hypotrichosis achieving at least a 1-grade improvement in GEA score when the bimatoprost-treated and vehicle-treated groups were compared: 74.3% vs. 13.6% (P<0.001) at month 4 and 77.7% vs. 13.6% (P<0.001) at month 6, respectively (Table 2). The differences in the corresponding responder rates for subjects with chemotherapy-induced hypotrichosis were not as pronounced due to natural eyelash regrowth in this subpopulation. However, this difference was statistically significant at month 6: 80.2% (bimatoprost 0.03%) vs. 51.5% (vehicle; P<0.001).

A marked increase was observed in the percentage of subjects in the idiopathic hypotrichosis subpopulation with at least a 3-point increase in ESQ Domain 2 at the 4- and 6-month time points when the groups receiving bimatoprost and vehicle were compared (Table IV). Although the corresponding responder rates for the chemotherapy-induced hypotrichosis subpopulation were higher in the bimatoprost-treated compared with vehicle-treated groups, the differences between these groups were not statistically significant at either month 4 or 6.

TABLE IV

Summary of improvements from baseline to months 4 and 6 for idiopathic hypotrichosis and chemotherapy-induced hypotrichosis subpopulations: efficacy endpoints based on GEA and/or ESQ scores (intent-to-treat population):

| Efficacy Endpoint[a] | Time Point | Idiopathic Hypotrichosis Bimatoprost (n = 179) Treatment Responders, n (%) | Idiopathic Hypotrichosis Vehicle (n = 59) Treatment Responders, n (%) | P-value[b] |
|---|---|---|---|---|
| Composite endpoint: ≥1-grade increase in GEA score and ≥3-point improvement in ESQ Domain 2 | Month 4[a] | 72 (40.2) | 4 (6.8) | <0.001 |
|  | Month 6 | 85 (47.5) | 2 (3.4) | <0.001 |
| ≥1-grade increase in GEA | Month 4 | 133 (74.3) | 8 (13.6) | <0.001 |
|  | Month 6 | 139 (77.7) | 8 (13.6) | <0.001 |

TABLE IV-continued

Summary of improvements from baseline to months 4 and 6 for idiopathic hypotrichosis
and chemotherapy-induced hypotrichosis subpopulations: efficacy endpoints based on GEA and/or
ESQ scores (intent-to-treat population):

| | | | | |
|---|---|---|---|---|
| ≥3-point increase in ESQ Domain 2 | Month 4 | 85 (47.5) | 9 (15.3) | <0.001 |
| | Month 6 | 100 (55.9) | 9 (15.3) | <0.001 |
| ≥2-grade increase in GEA Score | Month 4 | 46 (25.7) | 0 (0.0) | <0.001 |
| | Month 6 | 55 (30.7) | 0 (0.0) | <0.001 |

| | | Chemotherapy-Induced Hypotrichosis Subjects Receiving Bimatoprost (n = 96) Treatment Responders, n (%) | Chemotherapy-Induced Hypotrichosis Subjects Receiving Vehicle (n = 34) Treatment Responders, n (%) | P-value[b] |
|---|---|---|---|---|
| Composite endpoint: ≥1-grade increase in GEA score and ≥3-point improvement in ESQ Domain 2 | Month 4[a] | 36 (37.5) | 6[c] (18.2) | 0.041 |
| | Month 6 | 45 (46.9) | 6[c] (18.2) | 0.004 |
| ≥1-grade increase in GEA | Month 4 | 70 (72.9) | 18[c] (54.5) | 0.051 |
| | Month 6 | 77 (80.2) | 17[c] (51.5) | 0.001 |
| ≥3-point increase in ESQ Domain 2 | Month 4 | 39 (40.6) | 8[c] (24.2) | 0.092 |
| | Month 6 | 46 (47.9) | 12[c] (36.4) | 0.250 |
| ≥2-grade increase in GEA score | Month 4 | 35 (36.5) | 2[c] (6.1) | <0.001 |
| | Month 6 | 44 (45.8) | 3[c] (9.1) | <0.001 |

[a]Month 4 is the primary analysis time point;
[b]A Pearson's chi-square test is performed. If 25% or more of the cells have expected counts less than 5, then Fisher's exact test is used instead;
[c]Overall population of subjects with chemotherapy-induced hypotrichosis receiving vehicle is 33 subjects.
Bimatoprost: bimatoprost ophthalmic solution 0.03%.
ESQ, Eyelash Satisfaction Questionnaire;
GEA, Global Eyelash Assessment.

No subjects with idiopathic hypotrichosis receiving vehicle met the more stringent criteria of at least a 2-grade improvement in GEA score, although this rate was 25.7% (month 4) and 30.7% (month 6) in the bimatoprost-treated subjects (Table IV). Although the corresponding responder rates for subjects with chemotherapy-induced hypotrichosis receiving vehicle were higher (6.1% at month 4 and 9.1% at month 6), the higher eyelash regrowth rates in the bimatoprost-treated group were evident compared with the vehicle-treated group: 36.5% and 6.1% (P<0.001), respectively, at month 4.

Analysis of Eyelash Characteristics by Digital Imaging Analysis (DIA)

Representative subject photographs of eyelash growth in subjects with idiopathic hypotrichosis and chemotherapy-induced hypotrichosis after up to 6 months of treatment are shown in FIG. 12 (panels a and b, respectively). Statistically significant changes in the percentage improvement from baseline of eyelash length, thickness, and darkness were observed between bimatoprost-treated and vehicle-treated groups in both subpopulations at months 4 and 6 (Table V). However, month-6 measurements of eyelash characteristics of vehicle-treated post-chemotherapy subjects were similar to eyelash characteristics of subjects with idiopathic hypotrichosis at baseline indicating that natural eyelash regrowth in this subpopulation was insufficient at month 6.

TABLE V

Summary of improvements from baseline at months 4 and 6 for idiopathic hypotrichosis
and chemotherapy-induced hypotrichosis subpopulations: efficacy endpoints based on eyelash
characteristics (intent-to-treat population)

| | | Idiopathic Hypotrichosis[b] | | | Chemotherapy-Induced Hypotrichosis[b] | | |
|---|---|---|---|---|---|---|---|
| Efficacy Endpoint[a] | Time Point | Bimatoprost (n = 179), n (%) | Vehicle (n = 59), n (%) | P-value[c] | Bimatoprost (n = 96), n (%) | Vehicle (n = 34), n (%) | P-value[c] |
| Upper eyelash length (mm) | Month 4 | 22.9 (177) | -4.9 (58) | <0.001 | 28.5 (94) | 11.3 (31) | 0.022 |
| | Month 6 | 26.0 (177) | -1.0 (58) | <0.001 | 37.8 (94) | 16.3 (31) | 0.008 |
| Upper eyelash thickness (mm$^2$) | Month 4 | 95.9 (150) | -7.2 (52) | <0.001 | 180.1 (64) | 25.0 (19) | 0.002 |
| | Month 6 | 91.4 (150) | -7.7 (52) | <0.001 | 245.9 (64) | 33.3 (19) | 0.002 |

TABLE V-continued

Summary of improvements from baseline at months 4 and 6 for idiopathic hypotrichosis and chemotherapy-induced hypotrichosis subpopulations: efficacy endpoints based on eyelash characteristics (intent-to-treat population)

| Efficacy Endpoint[a] | Time Point | Idiopathic Hypotrichosis[b] | | | Chemotherapy-Induced Hypotrichosis[b] | | |
|---|---|---|---|---|---|---|---|
| | | Bimatoprost (n = 179), n (%) | Vehicle (n = 59), n (%) | P-value[c] | Bimatoprost (n = 96), n (%) | Vehicle (n = 34), n (%) | P-value[c] |
| Upper eyelash darkness[d] (intensity units) | Month 4 | −15.7 (150) | 1.4 (52) | <0.001 | −14.4 (65) | −5.7 (18) | 0.012 |
| | Month 6 | −14.1 (150) | 1.6 (52) | <0.001 | −16.3 (65) | −6.5 (18) | <0.001 |

[a]Month 4 is the primary analysis time point.
[b]Mean values are presented for the idiopathic hypotrichosis subpopulation. The median is reported for the chemotherapy-induced hypotrichosis subpopulation where the distribution of the values is skewed with a small number of very high values in percent change from baseline from those subjects who had very few or no eyelashes at baseline.
[c]P-value for between-group comparison is based on Wilcoxon rank-sum test.
[d]A negative change from baseline indicates darker eyelashes compared with baseline.
Bimatoprost: bimatoprost ophthalmic solution 0.03%.

Figure 13:
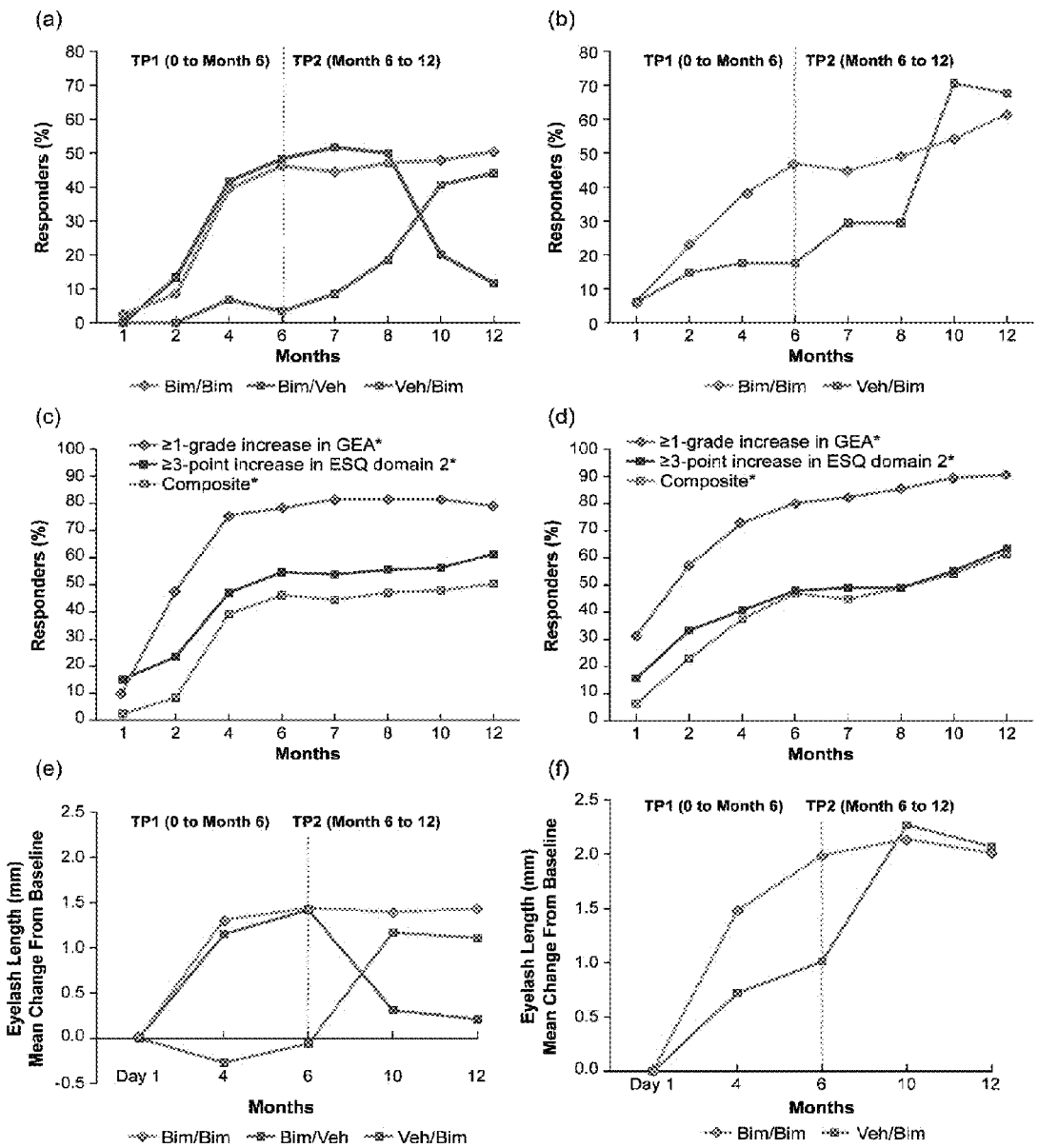

The improvement in eyelash prominence observed by month 4 or 6 of treatment were either maintained (idiopathic) or further enhanced (post-chemotherapy) through the 12-month period with once-daily treatment regimen (FIG. 13). FIG. 13 shows Responder rates for idiopathic hypotrichosis and chemotherapy-induced hypotrichosis subpopulations according to study treatments and time points. Panel a: Responder rates in subjects with idiopathic hypotrichosis treated with bimatoprost 0.03% or vehicle-primary composite efficacy measure; Panel b: responder rates in subjects with chemotherapy-induced hypotrichosis treated with bimatoprost 0.03% or vehicle-primary composite efficacy measure; Panel c: responder rates in subjects with idiopathic hypotrichosis treated with bimatoprost 0.03%-individual components of the primary composite efficacy measure; Panel d: responder rates in subjects with chemotherapy-induced hypotrichosis treated with bimatoprost 0.03%-individual components of the primary composite efficacy measure; Panel e: changes in eyelash length for subjects with idiopathic hypotrichosis; Panel f: changes in eyelash length for subjects with chemotherapy-induced hypotrichosis.

The effect of treatment discontinuation was studied in the idiopathic hypotrichosis subpopulation only. For subjects treated with bimatoprost during TP1 and switched to vehicle during TP2, the efficacy demonstrated at the end of TP1 was maintained through month 8, before diminishing at months 10 and 12 as demonstrated by the proportion of responders on the composite endpoint, and the efficacy endpoints based on components of the composite endpoint (Table VI).

TABLE VI

Summary of efficacy results for idiopathic hypotrichosis subjects treated with bimatoprost in treatment period 1 and switched to vehicle in treatment period 2 (intent-to-treat population)

| Efficacy Variable)Visit[a], n (%) | Treatment | Primary Composite Endpoint (n = 60) | ≥1-Grade Improvement From Baseline GEA Score (n = 60) | ≥3-Point Improvement From Baseline ESQ Domain 2 Score (n = 60) | ≥2-Grade Improvement From Baseline GEA Score (n = 60) |
|---|---|---|---|---|---|
| Month 1 | Bimatoprost | 0 (0.0) | 6 (10.0) | 8 (13.3) | 0 (0.0) |
| Month 2 | | 8 (13.3) | 24 (40.0) | 15 (25.0) | 2 (3.3) |
| Month 4 | | 25 (41.7) | 43 (71.7) | 29 (48.3) | 15 (25.0) |
| Month 6 | | 29 (48.3) | 46 (76.7) | 34 (56.7) | 18 (30.0) |
| Month 7 | Vehicle | 31 (51.7) | 47 (78.3) | 34 (56.7) | 18 (30.0) |
| Month 8 | | 30 (50.0) | 47 (78.3) | 33 (55.0) | 17 (28.3) |
| Month 10 | | 12 (20.0) | 28 (46.7) | 26 (43.3) | 5 (8.3) |
| Month 12 | | 7 (11.7) | 21 (35.0) | 23 (38.3) | 3 (5.0) |

Note:
Bim/Veh indicates the treatment group that received bimatoprost 0.03% during treatment period 1 and vehicle during treatment period 2.
[a]Visit was based on visit window. Baseline was defined as the most recent evaluation prior to day 1. Last observation carried forward was performed.
Bim/Veh: bimatoprost ophthalmic solution 0.03% during treatment period 1 followed by vehicle in treatment period 2. ESQ, Eyelash Satisfaction Questionnaire; GEA, Global Eyelash Assessment.

FIG. 13, panel a, illustrates the impact of treatment discontinuation at 6 months with the composite endpoint responder rate. Similar trends were observed with eyelash characteristics following treatment discontinuation with bimatoprost at 6 months (Table VII; FIG. 13, panel e).

TABLE VII

Summary of upper eyelash characteristics in idiopathic hypotrichosis subjects treated with bimatoprost in treatment period 1 and switched to vehicle in treatment period 2 (intent-to-treat population).

| Upper Eyelash Characteristics/Visit[a] | Treatment | Mean (Standard Deviation) at Baseline and Mean Value (Mean % Change From Baseline) | | |
|---|---|---|---|---|
| | | Length (mm) (n = 60) | Thickness (mm$^2$) (n = 60) | Darkness (intensity units)[b] (n = 60) |
| Baseline, mean (SD) | Bimatoprost | 5.7 (0.90) | 0.8 (0.32) | 152.5 (20.05) |
| Month 4, n (%) | | 6.8 (21.01) | 1.2 (73.7) | 126.3 (−16.01) |
| Month 6, n (%) | | 7.1 (25.70) | 1.2 (79.9) | 128.0 (−14.89) |
| Month 10, n (%) | Vehicle | 6.0 (6.46) | 0.8 (13.0) | 143.7 (−3.97) |
| Month 12, n (%) | | 5.9 (4.62) | 0.9 (15.9) | 143.6 (−4.29) |

Note:
Bim/Veh indicates the treatment group that received bimatoprost 0.03% during treatment period 1 and vehicle during treatment period 2.
[a]Visit was based on visit window. Baseline was defined as the most recent evaluation prior to day 1. Last observation carried forward was performed.
[b]The scale of intensity units is 0 to 255, where 0 is black and 255 is white. Therefore, lower values indicate darker eyelash color and higher values indicate lighter eyelash color, and negative changes from baseline indicate darker eyelashes compared with baseline.
Bim/Veh: bimatoprost ophthalmic solution 0.03% during treatment period 1 followed by vehicle in treatment period 2.

For subjects with idiopathic hypotrichosis treated with vehicle during TP1 and switched to bimatoprost for TP2, the bimatoprost treatment effect was observed during the same time in TP2 that had been observed for bimatoprost-treated subjects in TP1 (FIG. 13, panel a). Subjects with chemotherapy-induced hypotrichosis assigned to vehicle for TP1 followed by treatment with bimatoprost for TP2 demonstrated eyelash characteristics equal, or similar, to those subjects who received 12 months of treatment with bimatoprost (FIG. 13, panel f). These results indicate that bimatoprost solution 0.03% is an effective treatment for hypotrichosis of the eyelashes across both subpopulations, regardless whether it was started on day 1 or month 6 as well as the severity of the condition prior to treatment. It also indicates that early treatment (TP1) with bimatoprost 0.03% can achieve patient-desired results for eyelash growth sooner than would be achieved through natural regrowth or by starting later. Thus, the inclusion data of being at least 4 weeks post-chemotherapy-initiating therapy may be a reasonable time for physicians to start bimatoprost if such therapy is desired and warranted.

Safety Observations

A summary of the AEs occurring among at least 2% of subjects from either treatment group by treatment period and etiology subpopulation is shown in Table VIII.

TABLE VIII

Number of subjects treated with bimatoprost 0.03% for up to 12 months reporting adverse events (incidence of ≥2%) in the eye or skin system organ classes (safety population)

| | 0 to 12 Months | | 0 to 6 Months | | 6 to 12 Months | |
|---|---|---|---|---|---|---|
| System Organ Class Preferred Term[a] | Idiopathic Hypotrichosis (n = 118) | Chemotherapy-Induced Hypotrichosis (n = 96) | Idiopathic Hypotrichosis (n = 118) | Chemotherapy-Induced Hypotrichosis (n = 96) | Idiopathic Hypotrichosis (n = 106) | Chemotherapy-Induced Hypotrichosis (n = 89) |
| Eye disorders, n (%) | | | | | | |
| Conjunctival hyperaemia | 10 (8.5) | 16 (16.7) | 7 (5.9) | 15 (15.6) | 4 (3.8) | 1 (1.1) |
| Punctate keratitis | 3 (2.5) | 9 (9.4) | 3 (2.5) | 8 (8.3) | 0 (0.0) | 1 (1.1) |
| Eyelid pruritus | 7 (5.9) | 3 (3.1) | 6 (5.1) | 3 (3.1) | 1 (0.9) | 1 (1.1) |
| Erythema of eyelid | 6 (5.1) | 3 (3.1) | 2 (1.7) | 1 (1.0) | 5 (4.7) | 2 (2.2) |
| Eye pruritus | 1 (0.8) | 6 (6.3) | 1 (0.8) | 5 (5.2) | 0 (0.0) | 1 (1.1) |
| Skin and subcutaneous disorders, n (%) | | | | | | |
| Skin hyperpigmentation | 2 (1.7) | 5 (5.2) | 0 (0.0) | 3 (3.1) | 2 (1.9) | 2 (2.2) |

Bimatoprost ophthalmic solution 0.03% in each treatment period.
[a]Within each preferred term a subject was counted once for either treatment period or once for the entire treatment period.

The majority of AEs reported in the study were described as mild. There were no serious AEs attributed to study treatment. Ten subjects (2.8%) discontinued due to a treatment-related AE. All of these subjects were in the idiopathic hypotrichosis subpopulation. AEs leading to discontinuation in this subpopulation were conjunctival hyperaemia and erythema of eyelid (3 each), eye irritation (2), allergic conjunctivitis, enophthalmos (i.e., deepened eyelid sulcus), eye pruritus, dry eye, eyelid margin crusting, eyelid oedema, eyelid pruritus, and eyelid exfoliation (1 each). One subject discontinued due to decreased IOP, and another for contact dermatitis. The most frequently reported (≥2%) AEs for the overall population during bimatoprost treatment periods were conjunctival hyperaemia (12.1%), punctuate keratitis (5.6%), eyelid pruritus (4.7%), and erythema (4.2%). Most treatment-related AEs resolved without sequelae at the end of the study. One case of mild punctuate keratitis resolved with sequelae for which treatment and follow-up were deemed unnecessary; 1 case of madarosis was ongoing. A higher rate of conjunctival hyperaemia was noted in the chemotherapy-induced subpopulation (16.7%) compared with the idiopathic population (8.5%).

The percentage of subjects with biomicroscopy and ophthalmoscopy findings of at least a 2-severity grade increase from baseline for 1 or more visits during the bimatoprost treatment periods were 4.2% (9/214) for the group receiving bimatoprost during both treatment periods (12-month treatment period), 5.0% (3/60) for the group receiving bimatoprost 0.03% followed by vehicle (6-month treatment period), and 2.4% (2/84) for the group receiving vehicle followed by bimatoprost (6-month treatment period). No new safety signals arose in the second 6 months of treatment, indicating that longer-term treatment was not associated with an increased incidence of AEs. AEs of particular interest with prostamide F2α analogues include enophthalmos, IOP reduction, and iris hyperpigmentation.

Enophthalmos leading to treatment discontinuation occurred in only 1 bimatoprost-treated subject, and this was the only enophthalmos-related AE reported in the study. Reported as mild/moderate in severity, the onset of this AE was approximately 2 months after bimatoprost initiation. The AE was reported to be ongoing 6 months after the subject discontinued from the study.

The greatest magnitude of mean change from baseline IOP at any time point, for any group, was less than 2 mm Hg. The mean change from baseline in IOP was greater for bimatoprost-treated compared with vehicle-treated subjects with idiopathic hypotrichosis at all follow-up visits. These differences though statistically significant were considered not to be clinically relevant. At month 4, the mean change from baseline was −1.17 in the bimatoprost-treated subjects and 0.17 in the subjects receiving vehicle. In the chemotherapy-induced subpopulation, changes in IOP from baseline for the bimatoprost-treated subjects compared with vehicle-treated subjects were statistically significant at month 2 only; at the 2-month visit, the mean change from baseline was −1.22 and −0.14 in the bimatoprost-treated and vehicle-treated groups, respectively (P=0.022).

A 1-category change in iris hyperpigmentation was reported as an AE for only 1 subject in the study, occurring approximately 2 months after discontinuation of bimatoprost and initiation of vehicle. The AE was reported as mild in severity, with a color of blue-gray to blue/gray-brown, which was a 1-grade change on the 10-grade subjective classification. The subject did not discontinue from the study and the AE was reported to have resolved in a post-study communication. Resolution of iris hyperpigmentation is not typical of true prostaglandin-induced hyperpigmentation. For subjects treated with bimatoprost, there were reports of 5 subjects with a 1-category iris color change from light to dark; 6 subjects had iris color changes corresponding to a 1- to 2-category change in the direction of dark to light. In addition, iris color changes were reported in 2 subjects who had not received treatment with bimatoprost 0.03%. None of these color changes were considered to be clinically relevant. Some changes of 1 or 2 points on a 10-point scale are not unexpected from chance alone and may be, in part, consistent with less-than-perfect intra-rater reliability of the scale.

The AE profile demonstrated by this study was consistent with the known safety profile of bimatoprost solution 0.03%.

Discussion:

The composite efficacy endpoint used in this study, supported by the individual efficacy component measurements, provided for clinician and patient assessments of treatment results. In addition, DIA of eyelash characteristics allowed for an objective independent measure of treatment efficacy. Every group receiving bimatoprost in both subpopulations demonstrated statistically significant improvements from baseline compared with vehicle-treated control subjects for all efficacy endpoints after 4 months of treatment. These results were independent of whether treatment with bimatoprost was administered at baseline or delayed 6 months from baseline. This latter finding in the chemotherapy-induced hypotrichosis subpopulation indicated that bimatoprost can accelerate eyelash regrowth even when initiated months after chemotherapy cessation. In addition, for subjects in the groups receiving bimatoprost during both treatment periods, a more pronounced treatment effect from bimatoprost was observed in the chemotherapy-induced subpopulation compared with the idiopathic subpopulation at month 12. These results may be attributed to natural eyelash regrowth in subjects with chemotherapy-induced hypotrichosis in addition to the treatment effect of bimatoprost. However, month-6 measurements of mean eyelash characteristics of vehicle-treated subjects with chemotherapy-induced hypotrichosis were below mean eyelash characteristics of those with idiopathic hypotrichosis at baseline. Furthermore, about 80% of post-chemotherapy subjects were still nonresponders by the composite endpoint definition at month 6 suggesting that natural regrowth at 6 months is, in the vast majority of subjects, well below their desired and objective measures of growth. Thus, the natural eyelash regrowth following completion of chemotherapy appears to be a slow recovery process without intervention with bimatoprost.

The impact of bimatoprost discontinuation, evaluated in the idiopathic hypotrichosis subpopulation only, demonstrated that the treatment effect diminished after 2 months. These study findings are expected to be applicable to the chemotherapy-induced hypotrichosis subpopulation based on the similarities between the subpopulations, the known mechanism by which cytotoxic agents cause hair loss (i.e., no permanent damage to the hair follicle), and the putative mechanism of action of bimatoprost in stimulating hair growth following hair loss due to chemotherapy. However, whereas subjects with idiopathic hypotrichosis revert back to their baseline levels of eyelash prominence upon treatment discontinuation, the eyelash characteristics of subjects with chemotherapy-induced hypotrichosis would be expected to revert back to a level of prominence their eyelashes would naturally have achieved after chemotherapy cessation, and this result may be quite variable between individuals.

The majority of common AEs observed throughout the 12-month period occurred during the first 6 months of treatment, indicating that continuous long-term treatment does not lead to an increased incidence of AEs. In general, the AEs reported during this study were similar to those reported in previous studies of bimatoprost 0.03% for the treatment of hypotrichosis of the eyelashes; the AEs deemed by the investigator to be treatment related were largely localized to the treatment area, nonserious, mild in severity, reversible with treatment cessation, and predictable based on the known pharmacology of bimatoprost The incidences of treatment-related conjunctival hyperaemia, punctate keratitis, and eye pruritus were higher in the chemotherapy-induced hypotrichosis subpopulation than in the idiopathic hypotrichosis subpopulation. This difference may be due to the higher likelihood of eye conditions in a population with recent exposure to chemotherapeutic agents due to an effect of the chemotherapy. With respect to changes in IOP, it has been observed that IOP measurements in healthy subjects can vary by 3 to 6 mm Hg even throughout a single day. Thus, the mean changes in IOP were not considered clinically relevant in any treatment group. Similarly, the limited number of changes in iris color observed during the study was not considered clinically relevant, as most recorded changes were 1- or 2-category changes on a 10-category scale, and were transient. The reported changes are most likely attributable to assessment variability.

Conclusions:

Bimatoprost 0.03% application once daily over a 1-year period to the upper eyelids was found to be effective, safe, and well tolerated in subjects with idiopathic and chemotherapy-induced hypotrichosis. The primary treatment goals of these subpopulations are not identical since the subjects with chemotherapy-induced hypotrichosis seek to rapidly restore diminished eyelash prominence, a constant reminder of the disease, to their pre-chemotherapy state. Nevertheless, treatment with bimatoprost provided statistically significant and clinically meaningful benefits to both populations regardless of the severity of the condition prior to treatment. The AE profile demonstrated during this study was consistent with the previously reported safety profile of bimatoprost 0.03%. No new safety concerns were observed during the second 6-month treatment period compared with the safety profile observed in the first 6 months of treatment.

What is claimed is:

1. A method of growing eyelashes in chemotherapy patients, the method comprising applying 0.03% w/v bimatoprost at least once a day to the eyelids of a chemotherapy patient from at least one selected from the group consisting of before, during, and after chemotherapeutic treatment wherein patients receiving 0.03% w/v bimatoprost resulted in greater eyelash growth as compared to patients not receiving 0.03% w/v bimatoprost.

2. The method of claim 1, wherein 0.03% w/v bimatoprost is applied after chemotherapeutic treatment and results in greater eyelash growth in patients as compared to patients not receiving 0.03% w/v bimatoprost.

3. The method of claim 2, wherein the method results in eyelashes which are longer or thicker as compared to patients not receiving 0.03% w/v bimatoprost.

4. The method of claim 1, wherein the patients receiving 0.03% w/v bimatoprost before starting chemotherapeutic treatment resulted in greater eyelash growth as compared to patients receiving 0.03% w/v bimatoprost during or after chemotherapeutic treatment.

5. The method of claim 1, wherein 0.03% w/v bimatoprost is applied to the upper eyelid.

6. The method of claim 1, wherein 0.03% w/v bimatoprost is applied to the lower eyelid.

7. The method of claim 1, wherein the bimatoprost is added before, during and after chemotherapeutic treatment.

8. A method of treating eyelashes loss in chemotherapy patients, the method comprising applying 0.03% w/v bimatoprost at least once a day to the eyelids of a chemotherapy patient from at least one selected from the group consisting of before, during, and after chemotherapeutic treatment wherein patients receiving 0.03% w/v bimatoprost resulted in greater eyelash growth as compared to patients not receiving 0.03% w/v bimatoprost.

9. The method of claim 8, wherein 0.03% w/v bimatoprost is applied after chemotherapeutic treatment and results in greater eyelash growth in patients as compared to patients not receiving 0.03% w/v bimatoprost.

10. The method of claim 9, wherein the method results in eyelashes which are longer or thicker as compared to patients not receiving 0.03% w/v bimatoprost.

11. The method of claim 8, wherein the patients receiving 0.03% w/v bimatoprost before starting chemotherapeutic treatment resulted in greater eyelash growth as compared to patients receiving 0.03% w/v bimatoprost during or after chemotherapeutic treatment.

12. The method of claim 8, wherein 0.03% w/v bimatoprost is applied to the upper eyelid.

13. The method of claim 8, wherein 0.03% w/v bimatoprost is applied to the lower eyelid.

14. The method of claim 8, wherein the bimatoprost is applied after completing chemotherapeutic treatment.

15. The method of claim 14, wherein the method is applied for at least 12 months after completing chemotherapeutic treatment.

16. The method of claim 12 wherein the method is applied prior to receiving chemotherapeutic treatment.

17. The method of claim 16, wherein the method is applied for six months after receiving chemotherapeutic treatment.

18. The method of claim 8 wherein the bimatoprost is in the form of a solution or an emulsion.

19. The method of claim 8 wherein the bimatoprost is applied to the upper eyelid or both the upper and lower eyelid.

20. The method of claim 8 wherein the method is applied after the patient completes chemotherapeutic treatment.

* * * * *